(12) United States Patent
Kaesler et al.

(10) Patent No.: US 11,419,811 B2
(45) Date of Patent: Aug. 23, 2022

(54) MEANS AND METHODS FOR PREVENTING AND/OR TREATING CARIES

(71) Applicant: BASF SE, Ludwigshafen (DE)

(72) Inventors: Bruno Kaesler, Cuxhaven (DE); Rolf Knöll, Laudenbach (DE); Mewes Boettner, Berlin (DE); Eckhard Budde, Cologne (DE); Christine Lang, Berlin (DE); Martin Ryser, Dresden (DE); Markus Veen, Altmühldorf (DE)

(73) Assignee: BASF SE

( * ) Notice: Subject to any disclaimer, the term of this patent is extended or adjusted under 35 U.S.C. 154(b) by 115 days.

(21) Appl. No.: 16/580,658

(22) Filed: Sep. 24, 2019

(65) Prior Publication Data
US 2020/0085727 A1    Mar. 19, 2020

Related U.S. Application Data

(63) Continuation of application No. 15/602,475, filed on May 23, 2017, now abandoned, which is a continuation of application No. 13/462,171, filed on May 2, 2012, now abandoned, which is a continuation of application No. 11/662,347, filed as application No. PCT/EP2005/009724 on Sep. 9, 2005, now Pat. No. 8,192,978.

(60) Provisional application No. 60/608,381, filed on Sep. 10, 2004.

(30) Foreign Application Priority Data

Sep. 10, 2004    (EP) .................................. 04 02 1591

(51) Int. Cl.
| | |
|---|---|
| *A61K 8/99* | (2017.01) |
| *A23G 4/12* | (2006.01) |
| *A61Q 11/00* | (2006.01) |
| *C12N 1/20* | (2006.01) |
| *A23L 33/135* | (2016.01) |
| *A23G 3/36* | (2006.01) |
| *A61K 35/747* | (2015.01) |
| *A23K 50/10* | (2016.01) |

(Continued)

(52) U.S. Cl.
CPC ............... *A61K 8/99* (2013.01); *A23G 3/366* (2013.01); *A23G 4/123* (2013.01); *A23K 50/10* (2016.05); *A23K 50/30* (2016.05); *A23K 50/40* (2016.05); *A23K 50/50* (2016.05); *A23K 50/70* (2016.05); *A23K 50/75* (2016.05); *A23K 50/80* (2016.05); *A23L 7/10* (2016.08); *A23L 33/135* (2016.08); *A61K 8/0216* (2013.01); *A61K 8/042* (2013.01); *A61K 8/60* (2013.01); *A61K 35/747* (2013.01); *A61Q 11/00* (2013.01); *C12N 1/20* (2013.01); *C12N 1/205* (2021.05); *A23V 2002/00* (2013.01); *A23Y 2220/63* (2013.01); *A23Y 2220/73* (2013.01); *A23Y 2240/49* (2013.01); *C12R 2001/225* (2021.05)

(58) Field of Classification Search
None
See application file for complete search history.

(56) References Cited

U.S. PATENT DOCUMENTS

| | | |
|---|---|---|
| 4,746,512 A | 5/1988 | Kawai et al. |
| 6,872,565 B2 | 3/2005 | Mollstam et al. |

(Continued)

FOREIGN PATENT DOCUMENTS

| | | |
|---|---|---|
| EP | 1312667 A1 | 5/2003 |
| JP | 5632874 B2 | 11/2014 |
| WO | WO-2004/067729 A1 | 8/2004 |

OTHER PUBLICATIONS

Sookkhee, S1, M. Chulasiri, and W. Prachyabrued. "Lactic acid bacteria from healthy oral cavity of Thai volunteers: inhibition of oral pathogens." Journal of applied microbiology 90.2 (2001): 172-179. (Year: 2001).*

(Continued)

*Primary Examiner* — Emily A Cordas
(74) *Attorney, Agent, or Firm* — Faegre Drinker Biddle & Reath LLP

(57) ABSTRACT

The present invention relates to a microorganism belonging to the group of lactic acid bacteria characterized in that it is capable of specifically binding to *Streptococcus mutans*, wherein the specific binding is (i) resistant to heat treatment; and/or (ii) resistant to protease treatment; and/or (iii) calcium-dependent; and/or (iv) formed within a pH range between 4.5 and 8.5; and/or (v) formed in the presence of saliva. Preferably, the specific binding can be assayed as follows:
  (a) growing said microorganism to stationary phase;
  (b) mixing said microorganism with *Streptococcus mutans* which has been grown to stationary phase;
  (c) incubating the mixture obtained in step (b) under conditions allowing the formation of aggregates of said microorganism and *Streptococcus mutans* and
  (d) detecting aggregates by the occurrence of a pellet.
Another aspect of the present invention is an analog or fragment of said microorganism which is thermally inactivated or lyophilized, wherein said analog or fragment retains the capability of specifically binding to *Streptococcus mutans*. In addition, the present invention encompasses compositions and additives for food, feed or drinks comprising the microorganism belonging to the group of lactic acid bacteria which specifically bind to *Streptococcus mutans* or an analog or fragment thereof. Moreover, uses of said microorganism or said analog or fragment thereof for the preparation of an anticariogenic or pharmaceutical composition or anticariogenic food or feedstuff as well as methods for producing said compositions or food or feedstuff are provided by the present invention.

22 Claims, 2 Drawing Sheets

Figure 1:
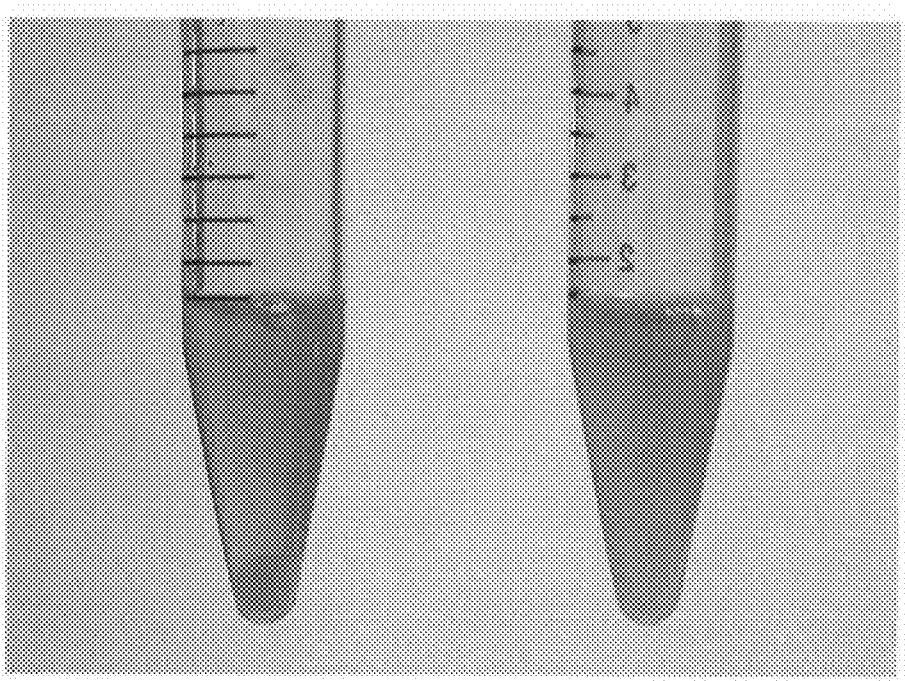

(51) Int. Cl.
| | |
|---|---|
| A23K 50/30 | (2016.01) |
| A23K 50/40 | (2016.01) |
| A23K 50/50 | (2016.01) |
| A23K 50/70 | (2016.01) |
| A23K 50/75 | (2016.01) |
| A23K 50/80 | (2016.01) |
| A23L 7/10 | (2016.01) |
| A61K 8/02 | (2006.01) |
| A61K 8/04 | (2006.01) |
| A61K 8/60 | (2006.01) |
| C12R 1/225 | (2006.01) |

(56) References Cited

U.S. PATENT DOCUMENTS

| | | |
|---|---|---|
| 7,189,390 B2 | 3/2007 | Zink et al. |
| 2004/0101495 A1 | 5/2004 | Nase et al. |
| 2004/0101496 A1 | 5/2004 | Chen |
| 2005/0180962 A1 | 8/2005 | Raz et al. |

OTHER PUBLICATIONS

Carlén, A., et al., "Saliva-Mediated Binding In Vitro and Prevalence In Vivo of *Streptococcus mutans*", Archives of Oral Biology, 1996, vol. 41, No. 1, pp. 35-39.

Communication Pursuant to Rule 62 EPC dated Aug. 20, 2010 Issued in European Application No. 10160493.2.

Dunkerson, D., et al., "Coaggregation of Mutants Streptococci with *S. sanguis* Cultured in Sucrose", J. Den. Res., 1993, vol. 72 (IADR Abstracts), p. 356 (Abstract No. 2025).

Gibbons, R. J., et al., "Interbacterial Aggregation of Plaque Bacteria", Archs. Oral Biol., 1970, vol. 15, pp. 1397-1400.

Kolenbrander, P. E., "Intergeneric Coaggregation Among Human Oral Bacteria and Ecology of Dental Plaque", Ann. Rev. Microbiol., 1998, vol. 42, pp. 627-656.

Otake, S., et al., "Protection of Rats Against Dental Caries by Passive Immunization with Hen-Egg-Yolk Antibody (IgY)", J. Dent. Res., 1991, vol. 70, No. 3, pp. 162-166.

Rose, R. K., "The Role of Calcium in Oral Streptococcal Aggregation and the Implications for Biofilm and Retention", Biochimica et Biophysica Acta, 2000, vol. 1475, pp. 76-82.

Shu, M., et al., "Development of Multi-Species Consortia Biofilms of Oral Bacteria as an Enamel and Root Caries Model System", Archives of Oral Biology, 2000, vol. 45, pp. 27-40.

Sookkhee et al., "Lactic Acid Bacteria from Healthy Oral Cavity of Thai Volunteers: Inhibition or Oral Pathogens", Journal of Applied Microbiology, 2001, vol. 90, pp. 172-179.

Carr, F. J., et al., "The Lactic Acid Bacteria: A Literature Survey", Critical Reviews in Microbiology, CRC Press, Inc., Boca Raton, Fl, US, vol. 28, No. 4, pp. 281-370, Dec. 11, 2002, XP009028374.

Chung, et al., "Isolation and Characterization of Lactobacilius Species Inhibiting the Formation of *Streptococcus mutans* Biofilm", Oral Microbiology Immunology, 2004, vol. 19, pp. 214-216.

Desmond, et al., Journal of Applied Microbiology, 2002, vol. 93, pp. 1003-1011.

Hamada, S., et al., "Oral Passive Immunization Against Dental Caries in Rats by Use of Hen Egg Yolk Antibodies Specific for Cell-Associated Glucosyltransferase of *Streptococcus mutans*", Infection and Immunity, 1991, vol. 59, No. 11, pp. 4161-4167.

Kruger, et al., Nature Biotechnology, 2002, vol. 20, pp. 702-706.

Kuramitsu, H. K., et al., "Interaction of *Streptococcus mutans* Glucosyltransferases with Teichoic Acids", Infection and Immunity, 1980, vol. 29, No. 2, pp. 376-382.

Notice of Reasons for Rejection dated Jan. 10, 2012 issued in JP Appl. No. 2007-530658 and the English translation thereof.

Ouwehand, et al., Letters in Applied Microbiology, 2000, vol. 31, pp. 82-86.

Rundegren, J., "Calcium-Dependent Salivary Agglutinin with Reactivity to Various Oral Bacterial Species", Infection and Immunity, 1986, vol. 53, No. 1, pp. 173-178.

Sharpe, M. E., et al., "Glycerol Teichoic Acid as a Common Antigenic Factor in Lactobacilli and Some Other Gram-positive Organisms", Journal of General Microbiology, 74, pp. 119-126, Jan. 1, 1973, XP055098050.

Wei, et al., "Stability and Activity os Specific Antibodies against *Streptococcus mutans* and *Streptococcus sobrinus* in Bovine Milk Fermented with Lactobacilius rhamnosus Strain GG or Treated at Ultra-High Temperature", Oral Microbiology Immunology, 2002, vol. 17, pp. 9-15.

Willcox, M. D. P., et al., "Coaggregation of Oral Lactobacilli with Streptococci from the Oral Cavity", Oral Microbiology and Immunology, 1993, vol. 8, pp. 319-321.

\* cited by examiner

MEANS AND METHODS FOR PREVENTING AND/OR TREATING CARIES

CROSS-REFERENCE TO RELATED APPLICATIONS

This application is a continuation of U.S. application Ser. No. 15/602,475, filed May 23, 2017, which is a continuation of U.S. application Ser. No. 13/462,171, filed May 2, 2012, which is a continuation of U.S. application Ser. No. 11/662,347, filed Feb. 14, 2008, all of which are incorporated by reference herein in their entirety. U.S. Ser. No. 11/662,347 is a national stage application (under 35 U.S.C. § 371) of PCT/EP2005/009724, filed Sep. 9, 2005, which claims benefit of European Patent Application No. 04021591.5, filed Sep. 10, 2004 and U.S. Provisional Application No. 60/608,381, filed Sep. 10, 2004, all of which are incorporated herein by reference in their entirety.

The present invention relates to a microorganism belonging to the group of lactic acid bacteria characterized in that it is capable of specifically binding to *Streptococcus mutans*, wherein the specific binding is (i) resistant to heat treatment; and/or (ii) resistant to protease treatment; and/or (iii) calcium-dependent; and/or (iv) formed within a pH range between 4.5 and 8.5; and/or (v) formed in the presence of saliva. Preferably, the specific binding can be assayed as follows:
(a) growing said microorganism to stationary phase;
(b) mixing said microorganism with *Streptococcus mutans* which has been grown to stationary phase;
(c) incubating the mixture obtained in step (b) under conditions allowing the formation of aggregates of said microorganism and *Streptococcus mutans* and
(d) detecting aggregates by the occurrence of a pellet.

Another aspect of the present invention is an analog or fragment of said microorganism which is thermally inactivated or lyophilized, wherein said analog or fragment retains the capability of specifically binding to *Streptococcus mutans*. In addition, the present invention encompasses compositions and additives for food, feed or drinks comprising the microorganism belonging to the group of lactic acid bacteria which specifically bind to *Streptococcus mutans* or an analog or fragment thereof. Moreover, uses of said microorganism or said analog or fragment thereof for the preparation of an anticariogenic or pharmaceutical composition or anticariogenic food or feedstuff as well as methods for producing said compositions or food or feedstuff are provided by the present invention.

*Streptococcus mutans* plays a central role in the development of caries. *S. mutans* metabolises sucrose to organic acids thereby developing an acidic micro environment. On the one hand, this provides an advantage for the less acidophilic, non-cariogenic oral plaque bacteria. On the other hand, the organic acids demineralise dental enamel, leading to cariotic lesions. Furthermore, *S. mutans* synthesises a non-water soluble glucan matrix which enforces the plaque and adds to the adherence of *S. mutans* to the tooth surface.

The role of further bacterial species that are connected to caries development like lactic acid bacteria or actinomycetes is not conclusive. These bacteria are often found in cariotic lesions, but only in association with *S. mutans*. To present knowledge, the presence of *S. mutans* is an indispensable condition of cariogenesis.

The initial binding of *S. mutans* to the surface of the teeth occurs via two mechanisms. The first mechanism is binding of *S. mutans* via the streptococcal antigen I/II (SA I/II) a surface protein also known by the synonyms B, IF, P1, SR, MSL-1 or PAc—to the pellicle, a layer of saliva proteins on the teeth surface. Antibodies against this protein have been shown to prevent the adhesion of *S. mutans* in vitro.

Accordingly, the streptococcal antigen (SA I/II) is a target for vaccination. In different recombinant combinations the complete antigen, the saliva binding region, the protein coupled to cholera toxin or expressed on the surface of an avirulent *Salmonella* strain a successful immunization of animals has been shown. This resulted in high IgA titers and a reduction of *S. mutans* colonization (Huang et al., Infect. Immun. 69 (2001), 2154-2161). Comparable results have been achieved using a DNA-vaccine coding for SA I/II (Fan et al., J. Dent. Res. 81 (2002), 784-787). Passive immunity has been achieved by recombinant expression of anti-SA I/11 antibodies on the surface of lactic acid bacteria. These lactobacilli aggregate *S. mutans* and administration of the bacteria to rats led to a reduction of caries development (Krueger et al., Nature Biotechnology 20 (2002), 702-706).

The most important binding partner of the streptococcal antigen is the salivary agglutinin, a protein similar to the lung glycoprotein gp-340 from the scavenger receptor cysteine-rich superfamily (Prakobphol et al., J. Biol. Chem. 275 (2000) 39860-39866).

The role of agglutinin in cariogenesis is not entirely understood so far. It can lead to the adhesion of *S. mutans* when present bound to surfaces, and it can lead to an aggregation of *S. mutans* when present in a soluble state. The latter might result in a removal of aggregated *S. mutans* from the mouth by saliva flow. A high agglutinin concentration in saliva leads in vitro to an increase in the adhesion of *S. mutans*, whereas in vivo there is no clear correlation between the agglutinin concentration in saliva and the risk for caries (Stenudd et al., J. Dent. Res. 80 (2001), 2005-2010). Monoclonal antibodies against agglutinin completely block the binding of *S. mutans* to saliva-coated hydroxyapatite in vitro and prevent the agglutinin dependent aggregation (Carlen and Olsson, J. Dent. Res. 74 (1995), 1040-1047; Carlen et al., J. Dent. Res. 77 (1998), 81-90). Brady et al., Infect. Immuno 60 (1992), 1008-1017 showed that the surface adhesion and the aggregation can be independently inhibited by different antibodies. This indicates that different epitopes of agglutinin are responsible for these two effects.

Other saliva proteins frequently connected to the development of caries are proline-rich proteins (PRPs). However, the role of these proteins in the adhesion of cariogenic bacteria is discussed controversially. These proteins are coded by two gene loci (PRH-1 and PRH-2) and occur in different variants that differ in only a few amino acids (PRP-1, PRP-2, PIF. Db-double band). These variants can be cleaved proteolytically, resulting in the so-called small PRPs (PRP-3, PRP-4. PIF-f and Db-f). PRPs mediate a strong binding of commensales like *Actinomyces naeslundii* or non-mutans streptococci. Interestingly, this binding takes place only after adhesion of the protein to the tooth surface, resulting in a conformational shift making the binding sites accessible. *S. mutans* is only weakly bound. The PRP-variant Db is of relevance for the effective binding of *S. mutans*. A high concentration of Db correlates with a high adhesion of *S. mutans* and a strong development of caries. A reduced part of PRP-Db of a high total PRP concentration correlates with a low development of caries (Stenudd et al., J. Dent. Res. 80 (2001), 2005-2010). It is unknown, if *S. mutans* binds directly to PRPs.

The second way of *S. mutans* to adhere to the tooth surface is via a sucrose dependent adhesion. *S. mutans* expresses three different glycosyltransferases (GTFs) that are capable of synthesizing the sugar polymer glucan. Glucans exist in a water soluble form (1-6 glycosidic linkage) and a non-soluble form called mutan (1-3 glycosidic linkage). Mutan cannot be degraded either by oral bacteria or by enzymes in saliva. It forms a sticky matrix within the dental plaque that is the basis for the sucrose dependent adhesion of S. mutans. The glycosyltransferases GTFB and GTFC, the prevalent enzymes responsible for mutan formation, are located on the cell surface of S. mutans. In contrast, the glycosyltransferase GTFD synthesises the soluble glucan and is secreted by S. mutans. Experiments using GTF deficient mutants of S. mutans show that an interaction of all three enzymes is necessary for a sucrose dependent adhesion (Ooshima et al., J. Dent. Res. 80 (2001), 1672-1677). Glycosyltransferases have an N-terminal sucrose binding site and a C-terminal glucan binding site. Antibodies against the enzyme or against the glucan binding site lead to an inhibition of the sucrose dependent adhesion of S. mutans. It has not been possible to block the N-terminal sucrose binding site using antibodies (Yu et al., Infect. Immun. 65 (1997), 2292-2298).

An inhibition of glycosyltransferases followed by a reduced adhesion of S. mutans can also be achieved by some flavonoids or terpenoids (US 2004/00571013) or propolis extracts (Duarte et al., Biol. Pharmacol. Bull. 26 (2003), 527-531).

Lactic acid bacteria named S11 have been found, that reduce mutan formation and, therefore, adherence of S. mutans in vitro. As described above, mutan formation is essential for S. mutans to adhere to the tooth surface. Accordingly, Chung et at (Oral Microbiol. Immunol. 19 (2004), 214-216) have found detached S. mutans cells when they have been incubated with the lactic acid bacteria of strain S11 which are said to reduce mutan formation. The binding of S. mutans to mutan occurs via bacterial binding proteins (glucan binding protein). The exact mechanism of this binding has to be determined (Sato et al., Infect. Immun. 65 (1997), 668-675).

The fungi Trichoderma harzianum and Penicillium purpurogenum produce homologous alpha-1,3-glucanases (Fuglsang et al., J. Biol. Chem. 275 (2000), 2009-2018). The use of Enterococcus, Lactobacillus and Lactococcus species effective against glucan production and plaque formation is described (U.S. Pat. No. 6,036,952). The mechanism of action has to be elucidated.

A further approach to inhibit caries is to neutralise the low pH in the plaque. Urea and arginine are components of saliva. Urea is present in concentrations of 3-10 mmol/L without major differences between caries free and caries affected persons.

The concentration of free arginine differs between 4 and 40 µmol/L. Caries free individuals have a higher average of free arginine concentrations in saliva than caries affected persons (van Wuyckhuyse et al., J. Dent. Res. 74 (1995), 686-690).

Some plaque bacteria like Streptococcus sanguis and Actinomyces naeslundi are capable of cleaving urea or arginine resulting in the formation of ammonia. The alkaline ammonium rises the pH of the plaque and therefore reduces caries (Curran et al., Appl. Environm, Microbiol. 61 (1995), 4494-4496; Morou-Bermudez and Burne, Infect. Immun. 68 (2000), 6670-6676). Accordingly, these bacteria are suggested to be used to treat caries. Another approach suggested for treating caries is that by proteolyses of PRP-1 and PRP-3 arginine rich peptides are created, that can, after further proteolysis by oral bacteria like S. sanguis, S. oralis and S. mitis, lead to a higher pH in the plaque. By application of a recombinant variant of these peptides, the sucrose dependent decrease of the pH is inhibited (Li et al., Infect. Immun. 68 (2000), 5425-5429). Moreover, it is described that by using a urea containing chewing gum after sucrose intake the drop of pH can be inhibited and, accordingly, for example, S. mutans may not contribute so much to caries.

However, as is evident from the above, the prior art provides recombinant microorganisms and/or live microorganisms for use in treating caries which may be harmful and which are not food grade organisms. Alternatively, the prior art provides agents which may not be stable enough for a prolonged period in the oral cavity to exert their potential anticariogenic effect. In addition, the agents of the prior art so far suggested to be useful for treating caries, e.g., enzyme preparations, chemical compounds, etc. may not be cold-stable, pH-stable and/or thermostable which renders them rather ineffective. Furthermore, some of them bear the risk of adverse side effects. For example, streptococcal antigens which are suggested to be used for vaccination against caries may cause severe problems associated with vaccination. To summarize, the prior art does not provide an agent which is not harmful for the subject in need of caries prophylaxis and/or treatment, which can be effectively and easily used for treating caries and which can be cheaply produced in large amounts. Hence, there is a need for an agent which fulfils the aforementioned desirable criteria and which is useful for preventing and/or treating caries.

It, thus, follows that the technical problem underlying the present invention is to comply with the needs described above. The solution to this technical problem is achieved by providing the embodiments characterized in the claims.

Accordingly, in a first aspect the present invention relates to a microorganism belonging to the group of lactic acid bacteria characterized in that it is capable of specifically binding to Streptococcus mutans, wherein the specific binding is resistant to heat treatment; and/or (ii) resistant to protease treatment; and/or
(iii) calcium-dependent; and/or
(iv) formed within a pH range between 4.5 and 8.5 and/or
(v) formed in the presence of saliva.

Preferably, the specific binding can be assayed as follows:

(a) growing said microorganism to stationary phase;
(b) mixing said microorganism with Streptococcus mutans which has been grown to stationary phase;
(c) incubating the mixture obtained in step (b) under conditions allowing the formation of aggregates of said microorganism and Streptococcus mutans; and
(d) detecting aggregates by the occurrence of a pellet.

The specific binding is preferably assayed as described in Example 3 herein below. Microorganisms belonging to the group of lactic acid bacteria are preferably mixed with S. mutans in volumetric ratios of 3:1 to 60:1 (S. mutans: lactobacilli). Both, the lactic acid bacteria and S. mutans are grown to stationary phase as described in Example 1. Preferably, the optical density is measured photometrically at a wavelength of 600 nm. The mentioned ratios correspond to a ratio of colony forming units from 1:50 to 1:2.5. Preferably, an $OD_{600}=1$ in 1 ml correlates to $3\times10^8$ colony forming units of S. mutans. Preferably, an $OD_{600}=1$ in 1 mL correlates to $7\times10^9$ colony forming units of lactobacilli of the present invention. Preferably, for assaying the aggregation reaction, the bacteria are in a volume of 2 ml in 15 ml FALCON™ centrifuge tubes. If necessary, the culture suspensions are diluted with PBS-butter to obtain volumetric ratios mentioned above, while keeping the final volume at 2 ml. Preferably, the mixture is vortexed for about 15 seconds and then left undisturbed for at least 5, 10, 15 minutes and more preferably for at least 20 minutes at room temperature, i.e. any temperature between 16° C. and 25° C. An aggregation is visible as an immediate turbity of the suspension and, after at least 20 minutes an aggregation is visible by aggregates that settle as a visible pellet (exemplarily shown in FIG. 1, left FALCON™ centrifuge tube), whereas non-*S. mutans* aggregating mixtures stay in suspension (exemplarily shown in FIG. 1, right FALCON™ centrifuge tube). As a control, self-aggregation of the respective lactic acid bacterium and the *S. mutans* strain can be assayed by omitting either *S. mutans* or the lactic acid bacterium.

Additionally, the specific binding does not require magnesium. This characteristic can be tested as described in the appended Examples.

All the above-mentioned characteristics render the microorganism of the present invention belonging to the group of lactic acid bacteria a suitable agent for preventing and/or treating caries which is caused by *S. mutans*. Accordingly, the microorganism of the present invention exerts an anti-cariogenic effect and is thus a useful agent for preventing and/or treating caries. "Caries" or "dental caries" or "cavity" are interchangeable terms for a chronic infectious disease associated with soft decayed area in a tooth which progressively leads to the death of a tooth. It usually occurs in children and young adults but can affect any person. It is the most important cause of tooth loss in younger people. Caries can be diagnosed by methods known in the art (see, for example, Angmar-Mansson and ten Bosch, Adv. Dent. Res. 7 (1993), 70-79)

The term "preventing caries" includes prophylaxis of caries. Accordingly, a subject who has never been encountered with *Streptococcus mutans*, the causative agent of caries, but is at a risk of being encountered, i.e. infected with *Streptococcus mutans* benefits, for example, from the compositions of the present invention which comprise the microorganism or a mutant or derivative of the present invention or an analog or fragment thereof as described herein insofar as said subject will not suffer from caries. Hence, the compositions of the present invention are, for example, useful for being administered to infants or children for prophylaxis of caries since the infant's oral cavity is normally free of *Streptococcus mutans*. However, the compositions of the present invention are not limited to administration to infants or children.

The term "treating caries" includes administration of the compositions of the present invention to a subject suffering from caries for the purpose of diminishing the amount of cells of *Streptococcus mutans* and/or for completely depleting *Streptococcus mutans* from the mouth, in particular from the oral cavity including teeth. Of course, after having been cured from *Streptococcus mutans*, it is envisaged that the respective subject has benefits from the compositions of the present invention as regards their prophylactic anti-caries effects exerted on *Streptococcus mutans*.

Optionally, the microorganism of the present invention is a probiotic microorganism which has, besides its anticariogenic effects, beneficial effects to the host organism to which it is administered. A "probiotic", by the generally accepted definition, is a "live microbial feed supplement which beneficially affects the host animal by improving its intestinal microbial balance". The microorganism of the present invention, if it has probiotic properties, may be included in functional or health food stuff which is described herein below.

*Streptococcus mutans* occurs as part of the normal flora in the mouth. It is involved in the cause of dental caries. Dental plaque adheres to the fissures and pits of the teeth adjacent to the gums. It consists initially of glycoprotein which is precipitated and is adsorbed onto the tooth enamel. Oral bacteria then become associated with the glycoprotein. Dietary sucrose is an important contributor to caries production, particularly if the sucrose is in the form of sticky sweet foods some of which can remain in the mouth for some time. The sucrose is thus more completely metabolised by *Streptococcus mutans* to form acid. Drinks which contain sucrose are swallowed and so the sucrose spends less time in the mouth. It is essential that dental plaque is controlled by the use of regular tooth-brushing and the use of toothpicks and dental floss. The addition of 1 ppm of fluoride to drinking water has proved very effective in reducing caries. The possibility of using a vaccine against *Streptococcus mutans* has been rejected. However, by the surprising finding of the present invention that naturally-occurring microorganisms belonging to the group of lactic acid bacteria preferably to the genus of *Lactobacillus* are capable of specifically binding to *Streptococcus mutans*, it is possible to effectively prevent and/or treat caries since the microorganisms of the present invention aggregate and flush away *Streptococcus mutans* due to, for example, salivary flow from the mouth including the tooth surface and the oral cavity. Accordingly, the present invention provides easily administrable bacteria which are food-grade organisms that may, in addition to their anticariogenic properties, be useful as probiotics.

When screening a private collection to identify microorganisms for the capability to bind to *Streptococcus mutans*, it was surprisingly found that naturally-occurring microorganisms belonging to the group of lactic acid bacteria, preferably to the genus of *Lactobacillus* are capable of specifically binding to *Streptococcus mutans* which is the causative agent of caries. By specifically binding to *Streptococcus mutans*, the microorganism belonging to the group of lactic acid bacteria, preferably to the genus of *Lactobacillus* disclosed herein, inter alia, bind to and aggregate *Streptococcus mutans* and thus, in consequence, flush away *Streptococcus mutans* by the natural flow of salivary, thereby preventing and/or treating caries. On top of this, the microorganisms of the present invention do preferably not bind other microorganisms present in the oral cavity which is described herein and in particular in Example 4 herein below. Thus, the microenvironment of the oral cavity is not disturbed since only *S. mutans* as the causative agent of caries is depleted. To the best knowledge, *S. mutans* does not have any beneficial effects to the oral cavity and, thus, its loss has no adverse effect to the respective host.

Strikingly, the specific binding of the microorganism, in particular of the *Lactobacillus* species disclosed herein to *Streptococcus mutans* is resistant to heat treatment and/or resistant to protease treatment. In addition, the specific binding is dependent on calcium and/or independent of magnesium and stable at an acidic point of 4.5 and it occurs in the presence of saliva which renders it in particular suitable for oral applications or as additive for food, feed or drinks which may contain higher concentrations of calcium, such as milk. Remarkably, thermally inactivated or lyophilised analogs or (a) fragment(s) of said microorganisms disclosed herein are still capable of specifically binding to *Streptococcus mutans*. This surprising effect is advantageous for using said analog(s) or fragment(s) of said microorganisms as well as mutants or derivatives thereof in compositions for use in the mammals, preferably, humans or animals to prevent and/or treat caries. In particular said analogs or fragments can be easily added to any composition, e.g. cosmetic or pharmaceutical composition, food or feedstuff or drinks and the like. Additionally, the production of such analogs or fragments is cheap and easy and they can be stored for prolonged periods of time without loosing their capability to specifically bind to *Streptococcus mutans*. A further advantage of the microorganism of the present invention is that it retains its capability to specifically bind to *S. mutans* if it is lyophilised or spray-dried or dried. This makes it a favourable ingredient for the compositions disclosed herein.

Other embodiments and advantages of the invention are set forth in part in the description herein, and in part, may be obvious from the description, or may be learned from the practice of the invention.

Before the present invention is described in detail, it is to be understood that this invention is not limited to the particular methodology, protocols, bacteria, vectors, and reagents etc. described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W. Nagel, B. and Kölbl, H. eds. (1995), Helvetica Chimica Acta, CH-4010 Basel, Switzerland). Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It must be noted that as used herein and in the appended claims, the singular forms "a", "an", and "the", include plural referents unless the context clearly indicates otherwise. Thus, for example, reference to "a reagent" includes one or more of such different reagents, and reference to "the method" includes reference to equivalent steps and methods known to those of ordinary skill in the art that could be modified or substituted for the methods described herein.

When used in the context of the present invention, the term "microorganism belonging to the group of lactic acid bacteria" or "microorganism of the present invention" encompasses (a) microorganism(s) which belong(s) to bacteria, in particular belonging to gram-positive fermentative eubacteria, more particularly belonging to the family of lactobacteriaceae including lactic acid bacteria. In addition, said term also encompasses derivatives or mutants or analogs or fragments, such as a membrane fraction as described herein, of said microorganism(s) which retain the capability to specifically bind to *S. mutans*. The terms "derivative", "mutants", "analogs" and "fragments" are described elsewhere herein. Lactic acid bacteria are from a taxonomical point of view divided up into the subdivisions of *Streptococcus, Leuconostoc, Pediococcus* and *Lactobacillus*. The microorganism of the present invention is preferably a *Lactobacillus* species. Members of the lactic acid bacteria group normally lack porphyrins and cytochromes, do not carry out electron-transport phosphorylation and hence obtain energy only by substrate-level phosphorylation. i.e. in lactic acid bacteria ATP is synthesized through fermentation of carbohydrates. All of the lactic acid bacteria grow anaerobically, however, unlike many anaerobes, most lactic acid bacteria are not sensitive to oxygen and can thus grow in its presence as well as in its absence. Accordingly, the bacteria of the present invention are preferably aerotolerant anaerobic lactic acid bacteria, preferably belonging to the genus of *Lactobacillus*.

The lactic acid bacteria of the present invention are preferably rod-shaped or spherical, varying from long and slender to short bent rods, are moreover preferably immotile and/or asporogenous and produce lactic acid as a major or sole product of fermentative metabolism. The genus *Lactobacillus* to which the microorganism of the present invention belongs in a preferred embodiment is divided up by the following characteristics into three major subgroups, whereby it is envisaged that the *Lactobacillus* species of the present invention can belong to each of the three major subgroups:

(a) homofermentative lactobacilli
 (i) producing lactic acid, preferably the L-, D- or DL-isomer(s) of lactic acid in an amount of at least 85% from glucose via the Embden-Meyerhof pathway;
 (ii) growing at a temperature of 45° C., but not at a temperature of 15° C.;
 (iii) being long-rod shaped; and
 (iv) having glycerol teichoic acid in the cell wall;

(b) homofermantative lactobacilli
 (i) producing lactic acid, preferably the L- or DL-isomer(s) of lactic acid via the Embden-Meyerhof pathway;
 (ii) growing at a temperature of 15° C., showing variable growth at a temperature of 45° C.;
 (iii) being short-rod shaped or coryneform; and
 (iv) having ribitol and/or glycerol teichoic acid in their cell wall;

(c) heterofermentative lactobacilli
 (i) producing lactic acid, preferably the DL-isomer of lactic acid in an amount of at least 50% from glucose via the pentose-phosphate pathway;
 (ii) producing carbondioxide and ethanol
 (iii) showing variable growth at a temperature of 15° C. or 45° C.;
 (iv) being long or short rod shaped; and
 (v) having glycerol teichoic acid in their cell wall.

Based on the above-described characteristics, the microorganisms of the present invention can be classified to belong to the group of lactic acid bacteria, particularly to the genus of *Lactobacillus*. By using classical systematics, for example, by reference to the pertinent descriptions in "Bergey's Manual of Systematic Bacteriology" (Williams & Wilkins Co., 1984), a microorganim of the present invention can be determined to belong to the genus of *Lactobacillus*. Alternatively, the microorganisms of the present invention can be classified to belong to the genus of *Lactobacillus* by methods known in the art, for example, by their metabolic fingerprint, i.e. a comparable overview of the capability of the microorganism(s) of the present invention to metabolize sugars or by other methods described, for example, in Schleifer et al., System. Appl. Microb., 18 (1995), 461-467 or Ludwig et al., System. Appl. Microb., 15 (1992), 487-501. The microorganisms of the present invention are capable of metabolizing sugar sources which are typical and known in the art for microorganisms belonging to the genus of *Lactobacillus*. In a preferred embodiment, however, the microorganism of the present invention has a metabolic fingerprint selected from the group consisting of:
(i) it metabolizes D-lactose, but not L-sorbose and/or D-saccharose and/or D-inuline,
(ii) it metabolizes inuline,
(iii) it metabolizes L-sorbose, but not 0-lactose and/or D-saccharose and/or inuline, and
(iv) it metabolizes L-sorbose, D-lactose and inuline.

Preferably, the microorganism of the present invention has a metabolic fingerprint selected from the group consisting of:
(i) it metabolizes D-lactose, but not L-sorbose, D-saccharose and inuline,
(ii) it metabolizes L-sorbose, 0-lactose and inuline, but not D-saccharose,
(iii) it metabolizes L-sorbose, but not D-lactose, D-saccharose and inuline, and
(iv) it metabolizes L-sorbose, D-lactose, D-saccharose, but not inuline.

Of course, the microorganism of the present invention is not limited to the metabolization of the sugars mentioned in the aforementioned metabolic fingerprint pattern, but may be capable of metabolizing further sugars which are commonly metabolized by *Lactobacillus* species.

The affiliation of the microorganisms of the present invention to the genus of *Lactobacillus* can also be characterized by using other methods known in the art, for example, using SDS-PAGE gel electrophoresis of total protein of the species to be determined and comparing them to known and already characterized strains of the genus *Lactobacillus*. The techniques for preparing a total protein profile as described above, as well as the numerical analysis of such profiles, are well known to a person skilled in the art. However, the results are only reliable insofar as each stage of the process is sufficiently standardized. Faced with the requirement of accuracy when determining the attachment of a microorganism to the genus of *Lactobacillus*, standardized procedures are regularly made available to the public by their authors such as that of Pot et al., as presented during a "workshop" organized by the European Union, at the University of Ghent, in Belgium, on Sep. 12 to 16, 1994 (Fingerprinting techniques for classification and identification of bacteria, SDS-PAGE of whole cell protein). The software used in the technique for analyzing the SDS-PAGE electrophoresis gel is of crucial importance since the degree of correlation between the species depends on the parameters and algorithms used by this software. Without going into the theoretical details, quantitative comparison of bands measured by a densitometer and normalized by a computer is preferably made with the Pearson correlation coefficient. The similarity matrix thus obtained may be organized with the aid of the UPGMA (unweighted pair group method using average linkage) algorithm that not only makes it possible to group together the most similar profiles, but also to construct dendograms (see Kersters, Numerical methods in the classification and identification of bacteria by electrophoresis, in Computer-assisted Bacterial Systematics, 337-368, M. Goodfellow, A. G. O'Donnell Ed., John Wiley and Sons Ltd, 1985).

Alternatively, the affiliation of said microorganisms of the present invention to the genus of *Lactobacillus* can be characterized with regard to ribosomal RNA in a so called Riboprinter®. More preferably, the affiliation of the newly identified species of the invention to the genus *Lactobacillus* is demonstrated by comparing the nucleotide sequence of the 16S ribosomal RNA of the bacteria of the invention, or of their genomic DNA which codes for the 16S ribosomal RNA, with those of other genera and species of lactic acid bacteria known to date. Another preferred alternative for determining the attachment of the newly identified species of the invention to the genus *Lactobacillus* is the use of species-specific PCR primers that target the 16S-23S rRNA spacer region. Another preferred alternative is RAPD-PCR (Nigatu et al. in Antonie van Leenwenhoek (79), 1-6, 2001) by virtue of that a strain specific DNA pattern is generated which allows to determine the affiliation of an identified microorganisms in accordance with the present invention to the genus of *Lactobacillus*. Further techniques useful for determining the affiliation of the microorganism of the present invention to the genus of *Lactobacillus* are restriction fragment length polymorphism (RFLP) (Giraffa et al., Int, J. Food Microbial. 82 (2003), 163-172), fingerprinting of the repetitive elements (Gevers et al., FEMS Microbial. Lett. 205 (2001) 31-36) or analysis of the fatty acid methyl ester (FAME) pattern of bacterial cells (Heyrman et al., FEMS Microbial. Lett. 181 (1991), 55-62). Alternatively, lactobacilli can be determined by lectin typing (Annuk et al., J. Med. Microbial. 50 (2001), 1069-1074) or by analysis of their cell wall proteins (Gatti et al., Lett. Appl. Microbial. 25 (1997), 345-348.

In accordance with the present invention, the microorganisms are preferably lactic acid bacteria belonging to the genus of *Lactobacillus*, more preferably *Lactobacillus* species as described herein. Even more preferably the *Lactobacillus* of the present invention is *Lactobacillus paracasei* or *Lactobacillus rhamnosus*. However, the *Lactobacillus* species are not limited thereto. In a particular preferred embodiment the microorganisms of the present invention are "isolated" or "purified". The term "isolated" means that the material is removed from its original environment, e.g. the natural environment if it is naturally occurring. For example, a naturally-occurring microorganism, preferably a *Lactobacillus* species, separated from some or all of the coexisting materials in the natural system, is isolated. Such a microorganism could be part of a composition, and is to be regarded as still being isolated in that the composition is not part of its natural environment.

The term "purified" does not require absolute purity; rather, it is intended as a relative definition. Individual microorganisms obtained from a library have been conventionally purified to microbiological homogeneity, i.e. they grow as single colonies when streaked out on agar plates by methods known in the art. Preferably, the agar plates that are used for this purpose are selective for *Lactobacillus* species. Such selective agar plates are known in the art.

In a particularly preferred embodiment of the present invention, the microorganism of the present invention is selected from the group consisting of *Lactobacillus paracasei* or *Lactobacillus rhamnosus* having DSMZ accession number DSM 16667 (*L. paracasei* ssp. *paracasei* Lb-Ob-K1), DSMZ accession number DSM 16668 (*L. paracasei* ssp. *paracasei* Lb-Ob-K2), DSMZ accession number DSM 16669 (*L. paracasei* ssp. *paracasei* Lb-Ob-K3), DSMZ accession number DSM 16670 (*L. paracasei* ssp. *paracasei* Lb-Ob-K4), DSMZ accession number DSM 16671 (*L. paracasei* ssp. *paracasei* Lb-Ob-K5), DSMZ accession number DSM 16672 (*L. rhamnosus* Lb-Ob-K6) and DSM accession number DSM 16673 (*L. rhamnosus* Lb-Ob-K7) or a mutant or derivative thereof, wherein said mutant or derivative retains the capability to specifically bind to *Streptococcus mutans*. The term "*Lactobacillus paracasei* or *Lactobacillus rhamnosus* having DSMZ accession number" relates to cells of a microorganism belonging to the species *Lactobacillus*

*paracasei* or *Latobacillus rhamnosus* deposited with the Deutsche Sammlung für Mikroorganismen and Zellkulturen GmbH ("DSMZ") on Aug. 26, 2004 and having the following deposit numbers DSM 16667, 16668, 16669, 16670, 16671, 16672 or 16673. The DSMZ is located at the Mascheroder Weg 1b, D-38124 Braunschweig, Germany. The aforementioned DSMZ deposits were made pursuant to the terms of the Budapest treaty on the international recognition of the deposit of microorganisms for purposes of patent procedure.

"A mutant or derivative" of the microorganism of the present invention, preferably of the deposited *Lactobacillus paracasei* or *Lactobacillus rhamnosus* cells has preferably the same characteristics as the respective deposited strains, i.e. it retains the capability to specifically bind to *Streptococcus mutans*, preferably with the binding characteristics as described hereinabove. For example, said derivative can be genetically engineered. In the context of the present invention the term "genetically engineered" is used in its broadest sense for methods known to the person skilled in the art to modify desired nucleic acids in vitro and in vivo such that genetic modifications are affected and genes are altered by recombinant DNA technology. Accordingly, it is preferred that said methods comprise cloning, sequencing and transformation of recombinant nucleic acids. For this purpose appropriate vectors including expression vectors for *Lactobacillus* species as, for example, described in EP-B1 506 789, EP-B1 316 677, EP-B1 251 064, EP-B1 218 230, EP-B1 133 046 or WO 89/01979.

Primers, enzymes, further host cells for cloning of intermediate constructs and the like can be used and are known by the skilled artisan. Preferably, genetically engineered mutants comprise cells of the microorganism of the present invention, preferably of the deposited *Lactobacillus* species harbouring recombinant nucleic acids either comprised in their bacterial chromosome or on (a) plasmid(s) or comprised in their bacterial chromosome and/or (a) plasmid(s). Said recombinant nucleic acids are preferably foreign to the microorganism of the present invention. By "foreign" it is meant that the polynucleotide or nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the polynucleotide may be either under the control of its own promoter or under the control of a heterologous promoter. The vector or nucleic acid molecule according to the invention which is present in the host cell may either be integrated into the genome of the host cell or it may be maintained in some form extrachromosomally. In this respect, it is also to be understood that the nucleic acid molecule of the invention can be used to restore or create a mutant gene via homologous recombination.

Plasmids may be low, medium or high copy number plasmids. Said genetically engineered mutants may harbour nucleic acids encoding a glucanase or mutanase which is capable of degrading the mutan specific 1,3-glycosidic bond of saccharose subunits. Fungal glucanases are, for example, described in Fuglsang et al., J. Biol. Chem. 275 (2000), 2009-2018. It is also envisaged that genetically engineered mutants comprise cells harbouring recombinant nucleic acids encoding antibodies which are preferably secreted or anchored in the bacterial cell wall. The term "antibody" encompasses intact antibodies as well as antibody fragments thereof, like, separated light and heavy chains, Fab, Fab/c, Fv, Fab', F(ab')2. The term "antibody" also comprises humanized antibodies, bifunctional antibodies and antibody constructs, like single chain Fvs (scFv) or antibody-fusion proteins. It is also envisaged in context of this invention that the term "antibody" comprises antibody constructs which may be expressed in cells of the derivative of the deposited microorganism of the present invention, e.g. antibody constructs which may be transformed via, inter glia, vectors by methods known in the art. It is in particular envisaged that such antibody constructs specifically recognize, for example, the streptococcal antigen I/II. Such an approach is, for example, described in Krueger et al., Nat. Biotechnol. 20 (2002), 702-706 or § ajgga, Biochim Biophys Acta 1626 (2003), 57-64.

Secretion of the expressed antibody is preferably achieved by operatively linking the nucleic acid encoding an antibody to a secretion signal sequence. Anchoring in the bacterial cell wall could be achieved by making use of the mechanism of the enzyme sortase. Namely, surface proteins of gram-positive bacteria are linked to the bacterial cell wall by a mechanism that involves cleavage of a conserved Leu-Pro-X-Thr-Gly (LPXTG) motif and that occurs during assembly of the peptidoglycan cell wall. Accordingly, the nucleic acid molecule encoding an antibody may be fused to a sequence encoding the aforementioned conserved motif which is used by sortase to anchor proteins in the bacterial cell wall.

It is also envisaged that the microorganism of the present invention, preferably the deposited *Lactobacillus* species be genetically modified to harbor a nucleic acid molecule encoding reuterin which is an antimicrobial substance effective, inter alia, against *Streptococcus mutans*. Reuterin is, for example, described in Talarico et al., Chemother. 33 (1989), 674-679.

A mutant of the microorganism of the present invention, preferably a mutant of the deposited *Lactobacillus* strains is preferably artificially mutated. In accordance with the present invention, the term "mutated" means (a) permanent modification(s) of genetic material, i.e. nucleic acids, caused, for example, naturally or by physical means or chemical compounds/substances/agents, such as EMS or ENU. Said modifications include point mutations, like transitions or transversions, deletion/insertion/addition of one or more bases within a nucleic acid/gene/chromosome thereby modifying the nucleic acid/gene/chromosome which can cause, inter alia, aberrant gene expression/transcription/translation or inactive gene products, constitutive active/inactive gene products leading to e.g. dominant-negative effects. Preferably, a mutation leads to in increased capability of specifically binding *Streptococcus mutans*. Thus, it is also preferred that the mutant cells of the deposited microorganism which harbour (a) mutation(s) in (a) desired gene(s) or in which (a) mutation(s) in (a) desired gene(s) is induced by methods known to the person skilled in the art. It is also known in the prior art that mutated or genetically engineered bacterial cells can be selected by any suitable method/phenotype. In the context of the present invention, a mutant having an increased capability to specifically bind to *Streptococcus mutans* can be tested in accordance with the methods described in the appended Examples. The term "mutant", however, also includes cells of the microorganism of the present invention, preferably cells of the deposited microorganism which harbour naturally-occurring, spontaneous mutations in their genome, i.e. bacterial chromosome. "Spontaneous mutations" are mutations that arise naturally, i.e., without direct genetic manipulation by man, or by exposure to a mutagen. Selection of spontaneous mutants can be accomplished by culturing the strain and selecting the desired variants by, for example, the variant bacterium's capability to show an improved Methods for selection of spontaneous mutants are well known in the art (see, for example, Sambrook. Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989)). For example, such mutations may occur during cultivation, for example, during the normal cell division process coupled with DNA replication or during passaging and/or preserving the mutant of the microorganism of the present invention.

The oral cavity is home to many different species of streptococci and it is not surprising, considering they share the same habitat, that they have many features in common. Thus, it is preferable that the microorganism of the present invention binds specifically to *Streptococcus mutans*. Accordingly, the term "specifically binding" in the context of the present invention means that the microorganism of the present invention, preferably a microorganism belonging to the genus of *Lactobacillus* binds to *Streptococcus mutans* but does not bind to most other, preferably to no other species belonging to the genus *Streptococcus*. Other species belonging to the genus of *Streptococcus* are those described in Example 4. Namely, the microorganism of the present invention does preferably not bind to bacteria belonging to the species of *Streptococcus salivarius*, preferably belonging to the subspecies *thermophilus*, to the species *Streptococcus oralis*, to the species *Streptococcus mitis* and/or to the species *Streptococcus sanguinis*. More preferably, it does not bind to *Streptococcus salivarius* ssp. *thermophilus* (identified by API® 50 CH strips (Biomerieux, France), *Streptococcus oralis* (DSMZ 20066), *Streptococcus oralis* (DSMZ 20395), *Streptococcus oralis* (DSMZ 20627), *Streptococcus mitis* (DSMZ 12643) and/or *Streptococcus sanguinis* (DSMZ 20567). In addition, said microorganism preferably does not bind to bacteria belonging to genera other than *Streptococcus*, e.g. belonging to the genus of *Staphylococcus*. More preferably, it does not bind to bacteria belonging to the species *Staphylococcus epidermidis*. Most preferably, it does not bind to *Staphylococcus epidermidis* (DSMZ 1798) and/or *Staphylococcus epidermidis* (DSMZ 20044)

For the test of specific binding, preferably each of the aforementioned oral bacteria are preferably mixed in a volumetric ratio of 3:1 with *Lactobacillus* cultures of the present invention and aggregation is preferably assayed as described herein and for example in Example 3.

It was shown that the *Lactobacillus paracasei*, preferably *L. paracasei* ssp. *paracasei* of the present invention does not aggregate any of the aforementioned oral bacterial belonging to the genus of *Streptococcus* and it does not bind the bacteria belonging to the genus of *Staphylococcus* mentioned herein above. The *Lactobacillus rhamnosus* strains of the present invention were shown to not aggregate all of the above mentioned *Streptococcus* and *Staphylococcus* species, apart from *Streptococcus salivarius* ssp. *thermophilus*. Preferably the term "specifically binding" also means that a microorganism of the present invention binds to such *Streptococcus mutans* strains which have the capability to be a cariogenic dental pathogen.

The specific binding reaction comprises binding and, preferably, aggregating *Streptococcus mutans* cells as described herein by the microorganism of the present invention in the mouth. This specific binding leads, in consequence, to flushing away the *Streptococcus mutans* cells by, for example, salivary flow or by a mouth rinse or mouth wash and the like as described herein. The mouth defines the oral cavity of mammals, preferably humans or animals such as pets, composed by the oral mucosa (gums, lips, cheeks, palate and floor of the mouth), the tongue and the teeth (including artificial structures). Preferably, the specific binding reaction of the microorganisms of the present invention to *Streptococcus mutans* prevents *Streptococcus mutans* cells from attaching to the surface of a tooth or teeth (or while not being bound by theory could lead to detachment of *Streptococcus mutans* cells from the surface of a tooth or teeth) In consequence, the specific binding reaction results in flushing away *Streptococcus mutans* cells out of the mouth, thereby diminishing the causative agent of caries and, thus, preventing and/or treating caries. It is believed that the microorganism of the present invention may bind specifically to the streptococcal antigen I/II which is also known as antigen B, IF, P1, SR, MSL-1 or PAc. However, the microorganism of the present invention may bind to any other protein or surface structure of *S. mutans*, thereby aggregating *S. mutans* and flushing it out of the oral cavity as described herein. It is known that *Streptococcus mutans* binds via said streptococcal antigen I/II to the pellicle. Accordingly, when the microorganism of the present invention may bind, for example, to said streptococcal antigen I/II, *Streptococcus mutans* is hampered to bind to the surface of teeth which thus helps to prevent and/or treat caries.

The pellicle is a clear, thin covering containing proteins and lipids (fats) found in saliva. It is formed within seconds after a tooth surface is cleaned. Pellicle formation is the first step in dental plaque formation. Dental plaque is a soft deposit that accumulates on the teeth. Plaque can be defined as a complex microbial community, with greater than $10^{10}$ bacteria per milligram. It has been estimated that as many as 400 distinct bacterial species may be found in plaque. In addition to the bacterial cells, plaque contains a small number of epithelial cells, leukocytes, and macrophages. The cells are contained within an extracellular matrix, which is formed from bacterial products and saliva. The extracellular matrix contains protein, polysaccharide and lipids. One of the proteins present in saliva is agglutinin which is on the one hand thought to lead to a partial removal of *Streptococcus mutans* from the mouth, however, is on the other hand suspected to facilitate adhesion of *Streptococcus mutans* to the surface of teeth, thereby facilitating the initial attachment of *Streptococcus mutans* to teeth and, thus, onset of caries.

Whether the microorganism of the present invention specifically binds to *Streptococcus mutans* as defined herein above can easily be tested, inter alia, by comparing the reaction of said microorganism of the present invention with *S. mutans* cells with a microorganism also belonging to the genus of *Lactobacillus* that does not specifically bind to *Streptococcus mutans* by preferably employing the method as described in the appended Examples herein below.

Preferably, the microorganism of the present invention is capable of specifically binding to *Streptococcus mutans* serotype c (DSMZ 20523) and/or serotype e (NCTC 10923) and/or serotype f (NCTC 11060). This means that the microorganism of the present invention binds to *Streptococcus mutans* serotype c, serotype e or serotype f. Preferably, this means that the microorganism of the present invention binds to *Streptococcus mutans* serotype c and serotype e or serotype f. This also means that the microorganism of the present invention binds to *Streptococcus mutans* serotype c and serotype f or serotype e or that the microorganism of the present invention binds to *Streptococcus mutans* serotype e and serotype f or c. More preferably this means that the microorganism of the present invention binds to *Streptococcus mutans* serotype c, serotype e and serotype f. In accordance with the present invention a "serotype" is an antigenic property of a bacterial cell, preferably of a *Streptococcus mutans* cell identified by serological methods known in the art.

As described above, the specific binding of the microorganism of the present invention to *Streptococcus mutans* is resistant to heat treatment. Accordingly, the microorganism of the present invention is treated with heat, for example, at a temperature above 15° C. or 37° C. More preferably, the cells are incubated at a temperature of more than 55° C., even more preferably of more than 65° C., particularly preferred of more than 95° C. and most preferred at 121° C. After cooling down, the capability of the microorganism of the present invention to specifically bind the *S. mutans* is determined as described herein.

The corresponding temperature can depend on the specific *Lactobacillus* species but can be easily determined by the skilled person by routine experimentation, e.g. by incubating the corresponding cells at different temperatures and determining the amount of *Lactobacillus* cells which is still capable of specifically binding to *Streptococcus mutans* by using methods as those shown in the examples herein. Generally, the heat treatment should last for a period of time of at least 1 minute. Preferably, the heat treatment lasts for a period of time of at least n minutes, wherein n is an integer in the range of 2 to 60, with n=20 being particularly preferred. However, there is in principle no upper limit for the time of incubation. However, it is preferably no longer than 4, 3, 2 or 1 hour(s). The most preferred heat treatment is at least 20 minutes at a temperature of 121° C. in a saturated steam having an atmospheric pressure of 2 bar. The most preferred heat treatment is considered as abolishing any function of a protein and of any vitality of cells which thus distinguishes the microorganism of the present invention from other microorganism in that it is still capable of the specifically binding to *S. mutans*. Hence, it is very useful for any food, feed, drink or composition of the present invention if it is desired that the microorganism should not be alive.

The specific binding of the microorganism of the present invention is furthermore characterized by its resistance to protease treatment which is treatment with a protease selected from the group consisting of pronase E, proteinase K, trypsin and chymotrypsin. These proteinases are proteases which show no specificity and, thus, are considered as degrading any protein being on the cell surface of a microorganism. Other proteases, which are known to have preferences for certain patterns of amino acid residues are elastase, thrombin, aminopeptidase I. carboxypeptidase, dostripain, endoproteinase, papain, pepsin or proteases. The latter proteases could also be used to test whether the specific binding of the microorganism of the present invention to *S. mutans* is resistant to the latter more specific proteases. Thus, after protease treatment which is described in the appended Examples, the microorganism of the present invention is still capable of specifically binding to *Streptococcus mutans*.

In addition, the specific binding of the microorganism of the present invention is furthermore characterized by its dependency on calcium. Preferably, the specific binding takes place in the presence of a concentration of calcium ions between 0.05 mM and 500 mM, preferably between 1 mM and 100 mM. Particularly preferred the calcium concentration is between 2 mM and 30 mM. The dependency of the specific binding on calcium can be tested as described in the appended Examples.

Moreover, the specific binding to the microorganism of the present invention is maintained over a pH range between 4.0 and 9.0, preferably between 4.0 and 7.0 In particular, the pH value at which the specific binding takes still place is preferably 4.5. Assaying of the maintenance of the specific binding over the pH range described above is shown in the appended Examples.

Furthermore, the specific binding is independent of magnesium. Thus, it is not necessary that magnesium ions or magnesium salts are present which is demonstrated in the appended Examples.

A still further characteristic of the specific binding is its occurrence in the presence of saliva. Saliva is an exogenous secrete which is synthesized by the salivary glands. It is a complex liquid containing, apart from about 99% water a multiplicity of organic and inorganic compounds. Physiological ingredients of saliva are, inter alia, enzymes, e.g., amylases, carboanhydrases, lysozyme, peroxidases or proteins, e.g., mucins, lactoferrin, proline-rich proteins, cystatines, histatines or statherines or soluble IgA. Thus, although a variety of potentially interfering substances are present in saliva, the specific binding of the microorganism of the present invention was not disturbed or hampered. For testing the specific binding in the presence of saliva, it is preferred that saliva is used which contains preferably the *Streptococcus* species described in Example 4 and/or the *Staphylococcus* species of Example 4. If, however, *Lactobacillus rhamnosus* species of the present invention are tested for specific binding to *S. mutans* in the presence of saliva, it is preferred that *Streptococcus salivarius* ssp. *thermophilus* is omitted. The specific binding is assayed as described herein.

The aforementioned characteristics of the microorganism of the present invention belonging to the group of lactic acid bacteria renders it to be a robust and effective agent for preventing and/or treating caries since it is mainly administered in various forms to the mouth including the oral cavity and teeth where, inter alia, saliva including certain proteases and low pH values after ingestion of carbohydrate containing food stuff is present. Moreover, the resistance to heat has beneficial effects in adding the microorganism of the present invention as additive to food stuff during the preparation of said food stuff. Namely, food stuff is often heat sterilized, precooked, pasteurized and the like which is detrimental for viability of microorganisms.

In another aspect the present invention relates to an analog or fragment of the microorganism of the present invention, which is thermally inactivated or lyophilized, wherein said analog or fragment retains the capability of specifically binding *Streptococcus mutans*.

According to the present invention the term "analog of the microorganism of the present invention" includes a dead or inactivated cell of the microorganism of the present invention, preferably of the *Lactobacillus* species disclosed herein which is no longer capable to form a single colony on a plate specific for microorganisms belonging to the genus of *Lactobacillus*. Said dead or inactivated cell may have either an intact or broken cell membrane. Methods for killing or inactivating cells of the microorganism of the present invention are known in the art. El-Nezami et al., J. Food Prot. 61 (1998), 466-468 describes a method for inactivating *Lactobacillus* species by UV-irradiation. Preferably, the cells of the microorganism of the present invention are thermally inactivated or lyophilised as described in the appended Examples. Lyophilization of the cells of the present invention has the advantage that they can be easily stored and handled while retaining their capability to specifically bind to *S. mutans*. Moreover, lyophilised cells can be grown again when applied under conditions known in the art to appropriate liquid or solid media. Lyophilization is done by methods known in the art. Preferably, it is carried out for at least 2 hours at room temperature, i.e. any temperature between 16° C. and 25° C. Moreover, the lyophilized cells of the microorganism of the present invention are stable for at least 4 weeks at a temperature of 4° C. so as to still specifically bind to *S. mutans* as is shown in Example 7 herein below. Thermal inactivation can be achieved by incubating the cells of the microorganism of the present invention for at least 2 hours at a temperature of 170° C. Yet, thermal inactivation is preferably achieved by autoclaving said cells at a temperature of 121° C. for at least 20 minutes in the presence of saturated steam at an atmospheric pressure of 2 bar. In the alternative, thermal inactivation of the cells of the microorganism of the present invention is achieved by freezing said cells for at least 4 weeks, 3 weeks, 2 weeks, 1 week, 12 hours, 6 hours, 2 hours or 1 hour at 20° C. It is preferred that at least 70%, 75% or 80%, more preferably 85%, 90% or 95% and particularly preferred at least 97%, 98%, 99% and more particularly preferred, 99.1%, 99.2%, 99.3%, 99.4%, 99.5%, 99.6%, 99.7%, 99.8% or 99.9% and most particularly preferred 100% of the cells of the analog of the microorganism of the present invention are dead or inactivated, however, they have still the capability to specifically bind to *S. mutans*. Whether the analog or fragment of the microorganism of the present invention is indeed dead or inactivated can be tested by methods known in the art, for example, by a test for viability.

The term "analog of the microorganism of the present invention" also encompasses lysates or fractions of the microorganism of the present invention, preferably of the *Lactobacillus* species disclosed herein. According to the present invention the term "lysate" means a solution or suspension in an aqueous medium of cells of the microorganism of the present invention that are broken. However, the term should not be construed in any limiting way. The cell lysate comprises, e.g., macromolecules, like DNA, RNA, proteins, peptides, carbohydrates, lipids and the like and/or micromolecules, like amino acids, sugars, lipid acids and the like, or fractions of it. Additionally, said lysate comprises cell debris which may be of smooth or granular structure. Methods for preparing cell lysates of microorganism are known in the art, for example, by employing French press, cells mill using glass or iron beads or enzymatic cell lysis and the like. In addition, lysing cells relates to various methods known in the art for opening/destroying cells. The method for lysing a cell is not important and any method that can achieve lysis of the cells of the microorganism of the present invention may be employed. An appropriate one can be chosen by the person skilled in the art, e.g. opening/destruction of cells can be done enzymatically, chemically or physically. Non-limiting examples for enzymes and enzyme cocktails are proteases, like proteinase K, lipases or glycosidases; non-limiting examples for chemicals are ionophores, detergents, like sodium dodecyl sulfate, acids or bases; and non-limiting examples of physical means are high pressure, like French-pressing, osmolarity, temperature, like heat or cold. Additionally, a method employing an appropriate combination of an enzyme other than the proteolytic enzyme, an acid, a base and the like may also be utilized. For example, the cells of the microorganism of the present invention are lysed by freezing and thawing, more preferably freezing at temperatures below −70° C. and thawing at temperatures of more than 30° C., particularly freezing is preferred at temperatures below −75° C. and thawing is preferred at temperatures of more than 35° C. and most preferred are temperatures for freezing below −80° C. and temperatures for thawing of more than 37° C. It is also preferred that said freezing/thawing is repeated for at least 1 time, more preferably for at least 2 times, even more preferred for at least 3 times, particularly preferred for at least 4 times and most preferred for at least 5 times.

Accordingly, those skilled in the art can prepare the desired lysates by referring to the above general explanations, and appropriately modifying or altering those methods, if necessary. Preferably, the aqueous medium used for the lysates as described is water, physiological saline, or a buffer solution. An advantage of a bacterial cell lysate is that it can be easily produced and stored cost efficiently since less technical facilities are needed.

According to the invention, lysates are also preparations of fractions of molecules from the above-mentioned lysates. These fractions can be obtained by methods known to those skilled in the art, e.g., chromatography, including, e.g., affinity chromatography, ion-exchange chromatography, size-exclusion chromatography, reversed phase-chromatography, and chromatography with other chromatographic material in column or batch methods, other fractionation methods, e.g., filtration methods, e.g., ultrafiltration, dialysis, dialysis and concentration with size-exclusion in centrifugation, centrifugation in density-gradients or step matrices, precipitation, e.g., affinity precipitations, salting-in or salting-out (ammoniumsulfate-precipitation), alcoholic precipitations or other protein chemical, molecular biological, biochemical, immunological, chemical or physical methods to separate above components of the lysates. In a preferred embodiment those fractions which are more immunogenic than others are preferred. Those skilled in the art are able to choose a suitable method and determine its immunogenic potential by referring to the above general explanations and specific explanations in the examples herein, and appropriately modifying or altering those methods, if necessary.

"A fragment of the microorganism of the present invention" encompasses any part of the cells of the microorganism of the present invention. Preferably, said fragment is a membrane fraction obtained by a membrane-preparation. Membrane preparations of microorganisms belonging to the genus of *Lactobacillus* can be obtained by methods known in the art, for example, by employing the method described in Rollan et al., Int. J. Food Microbial. 70 (2001), 303-307, Matsuguchi et al., Clin. Diagn, Lab. Immunol. 10 (2003), 259-266 or Stent z et al, Appl. Environ. Microbial. 66 (2000), 4272-4278 or Varmanen et al., J. Bacteriology 182 (2000), 146-154. Alternatively, a whole cell preparation is also envisaged. Preferably, the herein described derivative or fragment of the microorganism of the present invention retains the capability of specifically binding to *Streptococcus mutans* which is described in detail herein.

Another aspect of the present invention is a composition comprising a microorganism belonging to the group of lactic acid bacteria which is capable of specifically binding to *Streptococcus mutans* or a mutant, derivative, analog or fragment of this microorganism, Preferably, this microorganism is a microorganism of the present invention or a mutant or derivative thereof or said analog or fragment of said microorganism. In a preferred embodiment, said composition comprises a microorganism as described above in an amount between $10^2$ to $10^{12}$ cells, preferably $10^3$ to $10^8$ cells per mg in a solid form of the composition. Preferably, this microorganism is a microorganism of the present invention. In case of a liquid form of compositions, the amount of the microorganisms is between $10^2$ to $10^{13}$ cells per ml. However, for specific compositions the amount of the microorganism may be different as is described herein. A preferred composition of the present invention does not contain lactose in a range between 1% (w/w) and 6% (w/w). It is also preferred that the composition contains not more than 1% (w/w) lactose, e.g. it contains less than 1%, preferably less than 0.9% (w/w), 0.8% (w/w) lactose, etc. or that the composition contains more than 6%, 7%, 8% etc. (w/w) lactose. Alternatively, but also preferred is that the composition does not contain lactose.

In a still further aspect, the present invention provides a method for the production of an anticariogenic composition comprising the steps of formulating a microorganism belonging to the group of lactic acid bacteria which is capable of specifically binding to *Streptococcus mutans* or a mutant, derivative, analog or fragment of this microorganism with a cosmetically, orally or pharmaceutical acceptable carrier or excipient. Preferably, this microorganism is a microorganism of the present invention and the mutant, derivative, analog or fragment is one of those of the present invention. A preferred anticariogenic composition of the present invention does not contain lactose in a range between 1% (w/w) and 6% (w/w). It is also preferred that the composition contains not more than 1% (w/w) lactose, e.g. it contains less than 1%, preferably less than 0.9% (w/w), 0.8% (w/w) lactose, etc. or that the anticariogenic composition contains more than 6%, 7%, 8% etc. (w/w) lactose. Alternatively, but also preferred is that the anticariogenic composition does not contain lactose.

The term "composition", as used in accordance with the present invention, relates to (a) composition(s) which comprise(s) at least one microorganism or mutant or derivative as described above, preferably of the present invention or analog or fragment of said microorganism. It is envisaged that the compositions of the present invention which are described herein below comprise the aforementioned ingredients in any combination. It may, optionally, comprise at least one further ingredient suitable for preventing and/or treating caries. Accordingly, it may optionally comprise any combination of the hereinafter described further ingredients. The term "ingredients suitable for preventing and/or treating caries" encompasses compounds or compositions and/or combinations thereof which either inhibit the binding of *Streptococcus mutans* to the surface of teeth, to pellicles and/or which inactivate *Streptococcus mutans*. More preferably, said term encompasses compounds or compositions and/or combinations thereof which may inhibit the adhesion of *Streptococcus mutans* to the surface of teeth, inhibit the activity of glycosyltransferases of *Streptococcus mutans*, inhibit or inactivate *Streptococcus mutans*, inhibit the agglutinin-dependent binding of *Streptococcus mutans* and/or inhibit the saccharose-dependent binding of *Streptococcus mutans* as will be described below.

In particular, it is envisaged that the composition optionally further comprises compounds which inhibit the adhesion of *Streptococcus mutans* to the tooth surface. Accordingly, it is envisaged that such a compound is an inhibitor of the competence signal peptide (CSP) of *Streptococcus mutans*. Said inhibitor is described in CA 2,302,861 as being a derivative or fragment of said CSP which competitively inhibits binding of said CSP to its natural receptor, a histidine kinase receptor, or which is an antibody against said CSP. Said inhibitor prevents the development of a biofilm environment of dental plaque on the surface of teeth and, thus, prevents binding of *Streptococcus mutans*. Alternatively, the composition of the present invention may optionally further comprise polypeptide fragments of the *Streptococcus mutans* I/II antigen that are useful in treating and/or preventing dental caries. Such polypeptide fragments are described in U.S. Pat. No. 6,500,433. Namely, said polypeptide fragments may have the ability to adhere to the mammalian tooth surface by binding to agglutinin in a competitive manner with naturally occurring *Streptococcus mutans* antigen I/II, thus preventing or diminishing the adhesion of *S. mutans* to the tooth. Some of the peptides of U.S. Pat. No. 6,500,433 have been shown to inhibit adhesion of *S. mutans* to a tooth surface model (whole human saliva adsorbed to the wells of polystyrene microtitre plates or hydroxyapatite beads). Accordingly, U.S. Pat. No. 6,500,433 describes these peptides to comprise one or more adhesion sites and will adhere to a mammalian tooth in a competitive manner with naturally occurring SA I/II. Another optional ingredient of the composition of the present invention is the fimbrial-associated adhesion protein from *Streptocous mutans*, SmaA, or a fragment thereof as described in WO 00/66616. The SmaA protein which is involved in the present invention is an adhesion from fimbriae of *S. mutans* which mediates attachment of the bacteria to the salivary pellicle, believed to be via binding to the 52 kd salivary protein, amylase. The mature SmaA protein has a molecular weight of about 65 kilodaltons (kd) as measured on a reducing polyacrylamide gel, exhibits the ability to bind amylase, and is the major immunodominant fimbrial protein of *S. mutans*. Accordingy, SmaA is believed to compete with *Streptococcus mutans* for adhesion sites on the surface of teeth.

As described above, it is envisaged that compounds which inhibit *Streptococcus mutans* glycosyltransferase activity are optionally further comprised in the composition of the present invention. For example, US 2004/0057908 describes a mixture of terpenoids and flavonoids which inhibit the activity of said glycosyltransferases. Duarte et al., Biol. Pharm. Bull. 26 (2003), 527-531 describe a novel type of propolis and its chemical fractions on glycosyltransferases and on growth and adherence of *Streptococcus mutans*. Accordingly, said novel type of propolis and its chemical fractions are contemplated to be an optional further ingredient of the composition of the present invention. Koo et al., J. Antimicrob. Chemother. 52 (2003), 782789 describe that apigenin and tt-farnesol inhibit *Streptococcus mutans* biofilm accumulation and polysaccharide production. Hence, apigenein and tt-farnesol are contemplated to be optionally comprised in the composition of the present invention. Since carbohydrate fatty acid esters are described in Devulapalie et al., Carbohydr. Res. 339 (2004), 1029-1034 to effect glycosyltransferase activity, said carbohydrate fatty acid esters are contemplated to be optionally comprised in the composition of the present invention.

Direct inhibition of *Streptococcus mutans* is, for example, described in WO 2004/000222. Namely, genetically modified bacteriophages specific for *Streptococcus mutans* are used for treating bacterial caries caused by *Streptococcus mutans*. WO 2004/017988 describes a composition of biologically active protease and at least one biologically active glycosidase which is used for treating bacterial caries. Imazato et al., Biomaterials 24 (2003), 3605-3609 describes that methacryloyloxydodecylpyridinium bromide (MDPB) is useful for inhibiting growth of *Streptococcus mutans*. Accordingly, it is envisaged that the aforementioned compounds may optionally be further comprised in the composition of the present invention.

Bovine milk lactoferrin described by Mitoma et al., J. Biol. Chem. 276 (2001), 18060-18065 or extracts of *Helichrysum italicum* described by Nostra et al., Lett. Appl. Microbiol. 38 (2004), 423-427 which inhibit agglutinin-dependent or saccharose-dependent binding of *Streptococcus mutans* are contemplated to be optionally further comprised in the composition of the present invention.

Moreover, the composition of the present invention may optionally further comprise a mutanase (1,3-glucanase) which is, for example, described in DE2152520 or Fuglsang (2000), loc. cit. or an antibiotic against *Streptococcus mutans*, for example, those described in U.S. Pat. No. 6,342,386; 5,932,469; 5,872,001 or 5,833,958. In addition, it is noted that the composition of the present invention may optionally comprise one or more of the aforementioned optional ingredients which are suitable for preventing and/or treating caries. Thus, said composition may contain at least two, three, four, five, etc., i.e. "n" optional ingredients, wherein "n" is an integer greater than 2 which is not limited. Said optional ingredients may be combined in any possible combination.

The composition may be in solid, liquid or gaseous form and may be, inter alia, in the form of (a) powder(s), (a) tablet(s), (a) film preparation(s), (a) solution(s) (an) aerosol(s), granules, pills, suspensions, emulsions, capsules, syrups, liquids, elixirs, extracts, tincture or fluid extracts or in a form which is particularly suitable for oral administration.

Liquid preparations suitable for oral administration, for example syrups can be prepared, using water, conventional saccharides such as sucrose, sorbitol and fructose, glycols such as polyethylene glycol and propylene glycol, oils such as sesame seed oil, olive oil and soybean oil, antiseptics such as p-hydroxybenzoate ester, preservatives such as p-hydroxybenzoate derivatives, for example p-hydroxybenzoate methyl and sodium benzoate, and other materials such as flavors, for example strawberry flavor or peppermint.

Further, preparations suitable for oral administration, for example tablets, powders and granules can be produced, using conventional saccharides such as sucrose, glucose, mannitol, and sorbitol, starch such as potato, wheat and corn, inorganic materials such as calcium carbonate, calcium sulfate, sodium hydrogen carbonate, and sodium chloride, plant powders such as crystal cellulose, licorice powder and gentian powder, excipients such as pinedex, disintegrators such as starch, agar, gelatin powder, crystal cellulose, carmellose sodium, carmellose calcium, calcium carbonate, sodium hydrogen carbonate and sodium alginate, lubricants such as magnesium stearate, talc, hydrogenated vegetable oils, macrogol, and silicone oil, binders such as polyvinyl alcohol, hydroxypropyl cellulose, methyl cellulose, ethyl cellulose, carmellose, gelatin, and starch glue fluid, surfactants such as fatty acid ester, and plasticizers such as glycerin. A film preparation(s) can be prepared by methods known in the art. An example for the preparation of a film is given in Example 19 herein.

In case of ordinary oral administration, the dose of the microorganism or analog or fragment of the present invention could be (in dry weight) as described hereinabove with respect to the cell number or with respect to the mass, for example, 1 µg to 50 g, 1 µg to 10 g, 1 µg to 5 mg, 1 µg to 1 mg or any other weight per subject per day or in several portions daily. In case of dosing to non-human animals, further, the dose varies depending on the age and species of an animal and the nature or severity of the symptom thereof. Without any specific limitation, the dose for animals is 0.1 mg to 10 g per 1 kg body weight, preferably 1 mg to 1 g per 1 kg body weight once daily or in several portions daily. However, these doses and the number of dosages vary depending on the individual conditions.

Preferably, the composition of the present invention is a cosmetic composition further comprising a cosmetically acceptable carrier or excipient. More preferably, said cosmetic composition is a dentifrice, chewing gum, lozenge, mouth wash, mouse rinse or dental floss, which has an anticariogenic activity. A preferred cosmetic composition of the present invention does not contain lactose in a range between 1% (w/w) and 6% (w/w). It is also preferred that the cosmetic composition contains not more than 1% (w/w) lactose, e.g. it contains less than 1%, preferably less than 0.9% (w/w), 0.8% (w/w) lactose, etc. or that the cosmetic composition contains more than 6%, 7%, 8% etc. (w/w) lactose. Alternatively, but also preferred is that the cosmetic composition does not contain lactose.

The cosmetic composition of the present invention comprises the microorganism, mutant, derivative, analog or fragment thereof as described above in connection with the composition of the invention and further a cosmetically or orally acceptable carrier. Preferably, as mentioned in connection with the composition of the present invention the microorganism, mutant, derivative, analog or fragment thereof is a microorganism, mutant, derivative, analog or fragment of the present invention. Preferably the cosmetic composition of the present invention is for use in oral applications. Accordingly, it may be in the form of a toothpaste, dentifrice, tooth powder, topical oral gel, mouth rinse, denture product, mouth spray, lozenge, oral tablet, or chewing gum.

The term "orally or cosmetically acceptable carrier" as used herein means a suitable vehicle, which can be used to apply the present compositions to the oral cavity in a safe and effective manner. Such vehicle may include materials such as fluoride ion sources, additional anticalculus agents, buffers, other abrasive materials, peroxide sources, alkali metal bicarbonate salts, thickening materials, humectants, water, surfactants, titanium dioxide, flavor system, sweetening agents, xylitol, coloring agents, and mixtures thereof. The term "safe and effective amount" as used herein, means a sufficient amount to clean teeth and reduce stain/plaque/gingivitis/calculus without harming the tissues and structures of the oral cavity.

The pH of the present herein described compositions ranges preferably from about 3.0 to about 9.0, with the preferred pH being from about 5.5 to about 9.0 and the most preferred pH being 7.0 to about 8.5 or 9.0.

The cosmetical composition is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition may be a single phase oral composition or may be a combination of two or more oral compositions.

The term "dentifrice", as used herein, means paste, gel, or liquid formulations unless otherwise specified. The dentifrice composition may be in any desired form, such as deep striped, surface striped, multilayered, having the gel surrounding the paste, or any combination thereof. The dentifrice composition may be contained in a physically separated compartment of a dispenser and dispensed side-by-side. Dentifrice compositions are, for example, described in EP-B1 0 617 608.

Preferred dentifrice compositions are described in Examples 13 to 16. In addition to the above described components, the embodiments of this invention can contain a variety of optional dentifrice ingredients some of which are described below. Optional ingredients include, for example, but are not limited to, adhesives, sudsing agents, flavouring agents, sweetening agents, additional antiplaque agents, additional abrasives, and colouring agents. These and other optional components are further described, for example, in U.S. Pat. Nos. 5,004,597; 4,885,155; 3,959,458; and 3,937,807.

For example, the toothpaste may include surfactants, chelating agents, fluoride sources, teeth whitening actives and teeth color modifying substances, thickening agents, humectants, flavouring and sweetening agents, alkali metal bicarbonate salt, miscellaneous carriers and/or other active agents.

One of the preferred optional agents of the present invention is a surfactant, preferably one selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

Another preferred optional agent is a chelating agent such as tartaric acid and pharmaceutically-acceptable salts thereof, citric acid and alkali metal citrates and mixtures thereof. Chelating agents are able to complex calcium found in the cell walls of the bacteria. Chelating agents can also disrupt plaque by removing calcium from the calcium bridges, which help hold this biomass intact.

It is common to have an additional water-soluble fluoride compound present in dentifrices and other oral compositions in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. Nos. 3,535,421 and 3,678,154. Representative fluoride ion sources include stannous fluoride, sodium fluoride, potassium fluoride, sodium monofluorophosphate and many others. Stannous fluoride and sodium fluoride are particularly preferred, as well as mixtures thereof.

Teeth whitening actives that may be used in the oral care compositions of the present invention include bleaching or oxidizing agents such as peroxides, perborates, percarbonates, peroxyacids, persulfates, metal chlorites, and combinations thereof. Suitable peroxide compounds include hydrogen peroxide, urea peroxide, calcium peroxide, and mixtures thereof. A preferred percarbonate is sodium percarbonate. Other suitable whitening agents include potassium, ammonium, sodium and lithium persulfates and perborate mono- and tetrahydrates, and sodium pyrophosphate peroxyhydrate. Suitable metal chlorites include calcium chlorite, barium chlorite, magnesium chlorite, lithium chlorite, sodium chlorite, and potassium chlorite. The preferred chlorite is sodium chlorite. Additional whitening actives may be hypochlorite and chlorine dioxide.

In addition to bleaching agents as teeth whitening agents, teeth color modifying substances may be considered among the oral care actives useful in the present invention. These substances are suitable for modifying the color of the teeth to satisfy the consumer. These substances comprise particles that when applied on the tooth surface modify that surface in terms of absorption and, or reflection of light. Such particles provide an appearance benefit when a film containing such particles is applied over the surfaces of a tooth or teeth.

In preparing toothpaste or gels, it is necessary to add some thickening material to provide a desirable consistency of the composition, to provide desirable active release characteristics upon use, to provide shelf stability, and to provide stability of the composition, etc. Preferred thickening agents are carboxyvinyl polymers, carrageenan, hydroxyethyl cellulose, laponite and water soluble salts of cellulose ethers such as sodium carboxymethylcellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Another optional component of the topical, oral carriers of the compositions of the subject invention is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, and propylene glycol, especially sorbitol and glycerin.

Flavoring and sweetening agents can also be added to the compositions. Suitable flavoring agents include oil of wintergreen, oil of peppermint, oil of spearmint, clove bud oil, menthol, anethole, methyl salicylate, eucalyptol, cassia, 1-menthyl acetate, sage, eugenol, parsley oil; oxanone, alpha-irisone, marjoram, lemon, orange, propenyl guaethol, cinnamon, vanillin, thymol, linalool, cinnamaldehyde glycerol acetal known as CGA, and mixtures thereof. Flavouring agents are generally used in the compositions at levels of from about 0.001% to about 5%, by weight of the composition.

Sweetening agents which can be used include sucrose, glucose, saccharin, dextrose, levulose, lactose as described herein above, mannitol, sorbitol, fructose, maltose, xylitol, saccharin salts, thaumatin, aspartame, D-tryptophane, dihydrochalcones, acesulfame and cyclamate salts, especially sodium cyclamate and sodium saccharin, and mixtures thereof. A composition preferably contains from about 0.1% to about 10% of these agents, preferably from about 0.1% to about 1%, by weight of the composition.

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The present composition may contain from about 0.5% to about 30%, preferably from about 0.5% to about 15%, and most preferably from about 0.5% to about 5% of an alkali metal bicarbonate salt.

Water employed in the preparation of commercially suitable oral compositions should preferably be of low ion content and free of organic impurities. Water generally comprises from about 10% to about 50%, and preferably from about 20% to about 40%, by weight of the aqueous toothpaste compositions herein. These amounts of water include the free water which is added plus that which is introduced with other materials, such as with sorbitol. Titanium dioxide may also be added to the present composition.

Titanium dioxide is a white powder, which adds opacity to the compositions. Titanium dioxide generally comprises from about 0.25% to about 5% by weight of the dentifrice compositions.

The pH of the present compositions is preferably adjusted through the use of buffering agents. Buffering agents, as used herein, refer to agents that can be used to adjust the pH of the compositions to a range of about 4.5 to about 9.5, Buffering agents include monosodium phosphate, trisodium phosphate, sodium hydroxide, sodium carbonate, sodium acid pyrophosphate, citric acid, and sodium citrate. Buffering agents can be administered at a level of from about 0.5% to about 10%, by weight of the present compositions. The pH of dentifrice compositions is measured from a 3:1 aqueous slurry of dentifrice, e.g., 3 parts water to 1 part toothpaste.

Other optional agents that may be used in the present compositions include dimethicone copolyols selected from alkyl- and alkoxy-dimethicone copolyols, such as C12 to C20 alkyl dimethicone copolyols and mixtures thereof. Highly preferred is cetyl dimethicone copolyol marketed under the Trade Name ABIL® EM90. The dimethicone copolyol is generally present in a level of from about 0.01% to about 25%, preferably from about 0.1% to about 5%, more preferably from about 0.5% to about 1.5% by weight. The dimethicone copolyols aid in providing positive tooth feel benefits. Other useful carriers include biphasic dentifrice formulations such as those disclosed in U.S. Pat. Nos. 5,213,790; 5,145,666; 5,281,410; 4,849,213 and 4,528,180.

The present cosmetic compositions may also include other active agents, such as antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethyistearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215. Other antimicrobials such as copper bisglycinate, copper glysinate, zinc citrate, and zinc lactate may also be included. Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranses, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to anti-microbial properties. Such agents are disclosed in U.S. Pat. No. 2,946,725 and in U.S. Pat. No. 4,051,234. Other antimicrobial agents include chlorhexidine, triclosan, triclosan monophosphate, and flavor oils such as thymol. Triclosan and other agents of this type are disclosed in U.S. Pat. Nos. 5,015,466 and 4,894,220. These agents, which provide anti-plaque benefits, may be present at levels of from about 0.01% to about 5.0%, by weight of the dentifrice composition.

The term "chewing gum" as defined herein means a confectionery composition which is suitable for chewing and which comprises 2% or greater, by weight of the composition, of elastomer. Suitable lozenge and chewing gum components are, for example, disclosed in U.S. Pat. No. 4,083,955; 6,770,214 or 6,270,781. Preferred lozenges are those described in Examples 11 and 12. A preferred chewing gum composition is described in Example 17.

Compositions of the present invention preferably comprise an elastomer, or mixture of several different elastomers. Elastomeric materials are generally known in the art but illustrative examples include styrene-butadiene rubber (SBR); synthetic gums; polyisobutylene and isobutylene-isoprene copolymers; natural gums; chicle; natural rubber; jelutong; balata; guttapercha; lechi carpi; sorva; and mixtures thereof. Compositions of the present invention preferably comprise from about 2% to about 30%, more preferably from about 5% to about 25%, by weight, of elastomer. These levels are determined by the desired final texture of the chewing gum since when the total level of elastomer is below about 2% the base composition lacks elasticity, chewing texture, and cohesiveness whereas at levels above about 30% the formulation is hard, rubbery and maintains a tight chew. Elastomer solvents are also preferably present in compositions of the present invention since they aid softening of the elastomer component. Preferred examples of elastomer solvents for use herein include the pentaerythritol ester of partially hydrogenated wood rosin, pentaerythritol ester of wood rosin, glycerol ester of partially dimerized rosin, glycerol ester of polymerised rosin, glycerol ester of tall oil, wood or gum rosin, glycerol ester of partially hydrogenated rosin, methyl ester of partially hydrogenated rosin, and mixtures thereof. Compositions of the present invention preferably comprise from about 2% to about 50%, more preferably from about 10% to about 35%, by weight, of elastomer solvent.

Lozenges for use in accordance with this invention can be prepared, for example, by art-recognized techniques for forming compressed tablets where the disaccharide is dispersed on a compressible solid carrier, optionally combined with any appropriate tableting aids such as a lubricant (e.g., magnesium-stearate) and is compressed into tablets. The solid carrier component for such tableting formulations can be a saliva-soluble solid, such as a cold water-soluble starch or a monosaccharide, so that the lozenge will readily dissolve in the mouth to release the contained disaccharide acid in saliva solution for contact with and absorption by the oral/pharyngeal mucosa when the lozenge is held in the mouth. The pH of the above-described formulations can range from about 4 to about 8.5.

Lozenges for use in accordance with the present invention can also be prepared utilizing other art-recognized solid unitary dosage formulation techniques.

A mouth wash or mouth rinse of the present invention could preferably be as follows,

| A | Olium menthae | 1.2 parts |
| | Tinctura Arnicae | 3.0 parts |
| | Tincture Myrrhae | 3.0 parts |
| | Tween | 5.0 parts |
| B | Spiritus 90% | 50.0 parts |
| C | Sodium Benzoate | 0.2 parts |
| | Sweetening agent (e.g. aspartane) | 0.02 parts |
| | Agua destilata ad 100, | |

A is to be well mixed, B is added under stirring and C is added subsequently. The resulting clear liquid is to be filtered within 48 hours after preparation. Another preferred mouth wash is described in Example 18.

Regardless of the dosage form, liquid or solid, in one preferred embodiment of the present invention the dosage form is held in the patient's mouth for a period of time to promote contact of the microorganism or analog or fragment of a microorganism of the present invention with the patient's oral cavity.

Another preferred composition of the present invention is a pharmaceutical composition comprising the microorganism or a derivative or mutant or an analog or fragment thereof as described above in connection with the pharmaceutical composition further comprising a pharmaceutical acceptable carrier or excipient. Preferably, the microorganism, mutant, analog, derivative or fragment thereof is a microorganism, mutant, derivative or fragment of the present invention.

In addition, the present invention relates to the use of a microorganism or a derivative or mutant or an analog or fragment thereof as described above in connection with the composition of the present invention for the preparation of a composition, preferably a pharmaceutical or cosmetic compound for the prophylaxis against caries. Preferably, the microorganism, mutant, derivative, analog or fragment thereof is a microorganism, mutant, derivative or fragment of the present invention.

Pharmaceutical compositions comprise a therapeutically effective amount of a microorganism or derivative or mutant of the present invention or an analog or fragment of said microorganism of the present invention described in connection with the composition of the present invention and can be formulated in various forms, e.g. in solid, liquid, powder, aqueous, lyophilized form.

The pharmaceutical composition may be administered with a pharmaceutically acceptable carrier to a patient, as described herein. In a specific embodiment, the term "pharmaceutically acceptable" means approved by a regulatory agency or other generally recognized pharmacopoeia for use in animals, and more particularly in humans. A preferred pharmaceutical composition of the present invention does not contain lactose in a range between 1% (w/w) and 6% (w/w). It is also preferred that the pharmaceutical composition contains not more than 1% (w/w) lactose, e.g. it contains less than 1%, preferably less than 0.9% (w/w), 0.8% (w/w) lactose, etc. or that the pharmaceutical composition contains more than 6%, 7%, 8% etc. (w/w) lactose. Alternatively, but also preferred is that the pharmaceutical composition does not contain lactose.

The term "carrier" refers to a diluent, adjuvant, excipient, or vehicle with which the therapeutic is administered. Such a carrier is pharmaceutically acceptable, i.e. is non-toxic to a recipient at the dosage and concentration employed. It is preferably isotonic, hypotonic or weakly hypertonic and has a relatively low ionic strength, such as provided by a sucrose solution. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, malt, rice, flour, chalk, silica gel, sodium stearate, glycerol monostearate, talc, sodium ion, dried skim milk, glycerol, propylene, glycol, water, ethanol and the like. The excipient may contain lactose as described herein above; most preferably it is lactose-free. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, starch, magnesium stearate, sodium saccharine, cellulose, magnesium carbonate, etc. Examples of suitable pharmaceutical carriers are described in "Remington's Pharmaceutical Sciences" by E. W. Martin. Skim milk, skim milk powder, non-milk or non-lactose containing products may also be employed. The skim milk powder is conventionally suspended in phosphate buffered saline (PBS), autoclaved or filtered to eradicate proteinaceous and living contaminants, then freeze dried heat dried, vacuum dried, or lyophilized. Some other examples of substances which can serve as pharmaceutical carriers are sugars, such as glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry. extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as colouring agents, flavouring agents, lubricants, excipients, tabletting agents, stabilizers, anti-oxidants and preservatives, can also be present.

Preferably, the oral formulation contains lactose as described herein and is most preferably lactose-free. Various carriers and/or excipients suitable for oral administration which are well known in the art may be used for the purpose of this invention. The non-cariogenic composition may, if desired, further contain various known additives such as, for example, preservatives, hardening agents, lubricants, emulsifiers, stabilizers, essence and the like. Such compositions will contain a therapeutically effective amount of the aforementioned compounds, preferably in purified form, together with a suitable amount of carrier so as to provide the form for proper administration to the patient. The formulation should suit the mode of administration.

Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline.

The pharmaceutical composition of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant. Adjuvants may be selected from the group consisting of a chloroquine, protic polar compounds, such as propylene glycol, polyethylene glycol, glycerol, EtOH, 1-methyl L-2-pyrrolidone or their derivatives, or aprotic polar compounds such as dimethylsulfoxide (DMSO), diethylsulfoxide, di-n-propylsulfoxide, dimethylsulfone, sulfolane, dimethylformamide, dimethylacetamide, tetramethylurea, acetonitrile or their derivatives. These compounds are added in conditions respecting pH limitations. The composition of the present invention can be administered to a vertebrate. "Vertebrate" as used herein is intended to have the same meaning as commonly understood by one of ordinary skill in the art. Particularly, "vertebrate" encompasses mammals, and more particularly humans.

The term "administered" means administration of a therapeutically effective dose of the aforementioned composition. By "therapeutically effective amount" is meant a dose that produces the effects for which it is administered, preferably this effect is anticariogenic. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents maybe administered alone or in combination with other treatments.

The administration of the pharmaceutical composition can be done in a variety of ways as discussed above, including, but not limited to, orally, subcutaneously, intravenously, intra-arterial, intranodal, intramedullary, intrathecal, intraventricular, intranasally, intrabronchial, transdermally, intranodally, intrarectally, intraperitoneally, intramuscularly, intrapulmonary, vaginally, rectally, or intraocularly.

Preferably the administration is orally or buccal. The attending physician and clinical factors will determine the dosage regimen. As is well known in the medical arts, dosages for any one patient depends upon many factors, including the patient's size, body surface area, age, the particular compound to be administered, sex, time and route of administration, general health, and other drugs being administered concurrently. A typical dose can be, for example, in the range of 0.001 to 1000 µg; however, doses below or above this exemplary range are envisioned, especially considering the aforementioned factors.

The dosages are preferably given once a week, however, during progression of the treatment the dosages can be given in much longer time intervals and in need can be given in much shorter time intervals, e.g., daily. In a preferred case the immune response is monitored using herein described methods and further methods known to those skilled in the art and dosages are optimized, e.g., in time, amount and/or composition. Progress can be monitored by periodic assessment. The pharmaceutical composition of the invention may be administered locally or systemically. It is also envisaged that the pharmaceutical compositions are employed in co-therapy approaches, i.e. in co-administration with other medicaments or drugs, for example other drugs for preventing, treating or ameliorating caries which are described herein.

Another preferred composition of the present invention is a food or feed composition comprising a microorganims, mutant, derivative, analog or fragment thereof as described in connection with the composition of the present invention, further comprising an orally acceptable carrier or excipient. Preferably, the microorganism, mutant, derivative, analog or fragment thereof is a microorganism, mutant, derivative or fragment of the present invention.

"Food" or "feed" comprises any latable, palatable and/or drinkable stuff for mammals, for example, humans or animals, e.g., pets as described herein. Food and feedstuff is described herein elsewhere. An "orally acceptable carrier" is described herein above and is preferably not toxic and of food and/or feed grade. Yet, this term also encompasses the carriers mentioned in connection with the pharmaceutical composition of the present invention. A preferred food or feed composition of the present invention does not contain lactose in a range between 1% (w/w) and 6% (w/w). It is also preferred that the food or feed composition contains not more than 1% (w/w) lactose, e.g. it contains less than 1%, preferably less than 0.9% (w/w), 0.8% (w/w) lactose, etc. or that the food or feed composition contains more than 6%, 7%, 8% etc. (w/w) lactose. Alternatively, but also preferred is that the food or feed composition does not contain lactose.

The present invention provides furthermore the use of a microorganism or a derivative or mutant thereof or an analog or fragment disclosed in connection with the composition of the present invention herein for the preparation of an anticariogenic composition which is preferably a dentifrice, chewing gum, lozenge, mouth wash, mouse rinse or dental floss as described herein above. Preferably, the microorganism, mutant, derivative, analog or fragment thereof is a microorganism, mutant, derivative or fragment of the present invention.

Another aspect of the present invention is a method for the production of an anticariogenic composition comprising the steps of formulating a microorganism or derivative or mutant thereof or an analog or fragment of a microorganism described in connection with the composition of the present invention with a cosmetically, pharmaceutically or orally acceptable carrier or excipient. Preferably, the microorganism, mutant, derivative, analog or fragment thereof is a microorganism, mutant, derivative or fragment of the present invention.

A method for the production of an anticariogenic foodstuff or feedstuff wherein the method comprises the step of adding a microorganism or derivative or mutant or an analog or fragment thereof which are disclosed herein in connection with the composition of the present invention is also provided by the present application. Preferably, the microorganism, mutant, derivative, analog or fragment thereof is a microorganism, mutant, derivative or fragment of the present invention.

In accordance with the present invention, the term "foodstuff" encompasses all eatable and drinkable food and drinks. Accordingly, the microorganism or analog or fragment may be included in a food or drink. These are, for example, gum, spray, beverage, candies, infant formula, ice cream, frozen dessert, sweet salad dressing, milk preparations, cheese, quark, lactose-free yogurt, acidified milk, coffee cream or whipped cream and the like.

Milk-based products are envisaged within the framework of the invention. Milk is however understood to mean that of animal origin, such as cow, goat, sheep, buffalo, zebra, horse, donkey, or camel, and the like. The milk may be in the native state, a reconstituted milk, a skimmed milk or a milk supplemented with compounds necessary for the growth of the bacteria or for the subsequent processing of fermented milk, such as fat, proteins of a yeast extract, peptone and/or a surfactant, for example. The term milk also applies to what is commonly called vegetable milk, that is to say extracts of plant material which have been treated or otherwise, such as leguminous plants (soya bean, chick pea, lentil and the like) or oilseeds (colza, soya bean, sesame, cotton and the like), which extract contains proteins in solution or in colloidal suspension, which are coagulable by chemical action, by acid fermentation and/or by heat. Finally, the word milk also denotes mixtures of animal milks and of vegetable milks.

Where the microorganism or analog or fragment of this invention are added to yogurt and the like having similar contents, it is sufficient to add the microorganism of this invention at a concentration of about $10^5$-$10^7$ cells/ml. In such a case, it is possible to completely prevent or inhibit dental caries induced by cariogenic strains of *S. mutans* without significant side effect upon the quality of the drink per se.

Such food drink or feed can be produced by a general method for producing foods and drinks or feeds, including adding the active ingredient to a raw or cooked material of the food, drink or feed. The food, drink or feed in accordance with the present invention can be molded and granulated in the same manner as generally used for foods, drinks or feeds. The molding and granulating method includes granulation methods such as fluid layer granulation, agitation granulation, extrusion granulation, rolling granulation, gas stream granulation, compaction molding granulation, cracking granulation, spray granulation, and injection granulation, coating methods such as pan coating, fluid layer coating, and dry coating, puff dry, excess steam method, foam mat method, expansion methods such as microwave incubation method, and extrusion methods with extrusion granulation machines and extruders.

The food, drink or feed according to the present invention includes foods, drinks or feeds comprising the active ingredient. The food, drink or feed to be used in the present invention includes any food, drink or feed. The active ingredient in the food, drink or feed is not specifically limited to any concentration as long as the resulting food, drink or feed can exert its activity of specifically binding to *Streptococcus mutans*. The concentration of the active ingredient is preferably 0.001 to 100% by weight, more preferably 0.01 to 100% by weight and most preferably 0.1 to 100% by weight of the food, drink or feed comprising such active ingredient or with respect to the cell number those described herein.

Specific foods or drinks, to which the active ingredient is added, include, for example, juices, refreshing drinks, soups, teas, sour milk beverages, dairy products such as fermented milks, ices, butter, cheese, processed milk and skim milk, meat products such as ham, sausage, and hamburger, fish meat cake products, egg products such as seasoned egg rolls and egg curd, confectioneries such as cookie, jelly, snacks, and chewing gum, breads, noodles, pickles, smoked products, dried fishes and seasonings. The form of the food or drink includes, for example, powder foods, sheet-like foods, bottled foods, canned foods, retort foods, capsule foods, tablet foods and fluid foods.

The food or drink with an activity to specifically bind to *Streptococcus mutans* to be ingested by infants, are preferably nutritious compositions for infants. Such nutritious composition for infants includes modified milk prepared for infants, protein-decomposed milk, specific nutritionally modified milk or baby foods and foods prepared for toddlers. The form of the nutritious composition for infants includes but is not specifically limited to powder milks dried and pulverized and baby foods and also include general foods such as ice cream, fermented milk, and jelly for infantile ingestion.

The nutritious composition for infants in accordance with the present invention is principally composed of protein, lipid, saccharide, vitamins and/or minerals. In the nutritious composition, the active ingredient is blended with these components.

The protein includes milk proteins such as skim milk, casein, cheese whey, whey protein concentrate and whey protein isolates and their fractions such as alpha s casein, beta-casein, alpha-lactoalbumin and beta-lactoglobulin. Further, egg protein such as egg yolk protein, egg white protein, and ovalbumin, or soybean protein such as defatted soybean protein, separated soybean protein, and concentrated soybean protein can be used. Other than these, proteins such as wheat gluten, fish meat protein. cattle meat protein and collagen may also be used satisfactorily. Further, fractions of these proteins, peptides from the acid or enzyme treatment thereof, or free no acids maybe used satisfactorily as well. The free amino acids can serve as nitrogen sources and can additionally be used to give specific physiological actions. Such free amino acids include, for example, taurine, arginine, cysteine, cystine and glutamine. The lipid includes animal fats and oils such as milk. fat, lard, beef fat and fish oil, vegetable oils such as soybean oil. rapeseed oil, corn oil, coconut oil, palm oll, palm kernel oil, safflower oil, perilla oil, linseed oil, evening primrose oil, medium chain fatty acid triglyceride, and cotton seed oil, bacterially generated fats and oils, and fractionated oils thereof, hydrogenated oils thereof, and ester exchange oils thereof. The amount of lipid to be blended varies depending on the use.

The saccharide includes, for example, one or more of starch, soluble polysaccharides, dextrin, monosaccharides such as sucrose, lactose as described herein, maltose, glucose, and fructose and other oligosaccharides. The total amount of such saccharide is preferably 40 to 80% by weight to the total solid in the nutritious composition. Further, artificial sweeteners such as aspartame may be used satisfactorily. The amount of an artificial sweetener is appropriately 0.05 to 1.0% by weight per the total solid in the nutritious composition.

The vitamins include, but are not limited to, lycopene as an essential component and additionally include, for example, vitamins such as vitamin A, vitamin B group, vitamins C, D, and E and vitamin K group, folic acid, pantothenic acid, niootinamide, carnitine, choline, inositol and biotin as long as such vitamins can be administered to infants. Such vitamins are preferably from 10 mg to 5 g by weight per the total solid in the nutritious composition for infants.

Further, the minerals include calcium, magnesium, potassiw, sodium, iron, copper, zinc, phosphorus, chlorine, manganese, selenium and iodine. Such minerals are preferably from 1 mg to 5 g by weight per the total solid in the nutritious composition for infants.

Other than those components described above, the nutritious composition for infants of the present invention may be blended with any component desirably blended in nutritious compositions, for example, dietary fiber, nucleotides, nucleic acids, flavors, and colorants.

The food or drink of the present invention can be used as a health food or drink or a functional food or drink to prevent and/or treat caries.

When the food or drink according to the present invention is ingested, the amount to be ingested is not specifically limited. The amount to be ingested is generally 0.1 to 50 g, preferably 0.5 g to 20 g daily, based on the total amount of active ingredient. The food or drink is continuously ingested at this amount for a period from a single day up to 5 years, preferably from 2 weeks to one year. Herein, the amount ingested can be adjusted to an appropriate range depending on the severity of the symptom of the individual ingesting the food or drink, the age and body weight thereof, and the like.

The feed of the present invention maybe any feed comprising the active ingredient. The feed includes, for example, pet feeds for dogs, cats and rats, cattle feeds for cows and pigs, chicken feeds for chicken and turkeys, and fish cultivation feeds for porgy and yellowtail.

The feed can be produced by appropriately blending the active ingredient of the present invention in a raw feed material including, for example, cereals, brans, oil-seed meals, animal-derived raw feed materials, other raw feed materials and purified products.

The cereals include, for example, mile, wheat, barley, oats, rye, brown rice, buckwheat, fox-tail millet, Chinese millet, Deccan grass, corn, and soybean.

The brans include, far example, rice bran, defatted rice bran, bran, lowest-grade flour, wheat germ, barley bran. screening pellet, corn bran, and corn germ.

The oil-seed meals include, for example, soybean meal, soybean powder, linseed meal, cottonseed meal, peanut meal, safflower meal, coconut meal, palm meal, sesame meal, sunflower meal, rapeseed meal, kapok seed meal and mustard meal.

The animal-derived raw feed materials include, for example, fish powders, import meal, whole meal, and coast meal, fish soluble, meat powder, meat and bone powder, blood powder, decomposed hair, bone powder, byproducts from butchery, feather meal, silkworm pupa, skim milk, casein, dry whey and krill.

Other raw feed materials include, for example, plant stems and leaves such as alfalfa, hey cube, alfalfa leaf meal, and locust leaf powder, byproducts from corn processing industries, such as corn gluten meal, corn gluten feed and corn steep liquor, starch, sugar, yeast, byproducts from fermentation industry such as beer residue, malt root, liquor residue and soy sauce residue, and agricultural byproducts such as citrus processed residue, soybean curd residue, coffee residue, and cocoa residue, cassava, horse bean, guar meal, seaweed, spirulina and chlorella.

The purified products include, for example, proteins such as casein and albumin, amino acids, starch, cellulose, saccharides such as sucrose and glucose, minerals and vitamins, In case of providing to animals the feed according to the present invention, the amount of the feed to be ingested is not specifically limited but is preferably, for example, 0.1 mg to 50 g per I kg body weight per day, preferably 0.5 mg to 20 g per 1 kg body weight per day, based on the amount of the active ingredient. The feed is continuously ingested at this amount for a period from a single day up to 5 years, preferably from 2 weeks to one year. Again, the amount ingested can be adjusted to an appropriate range depending on the species, age and body weight of the animal ingesting the feed, and the like.

Furthermore, the present invention relates to an additive for foods, drinks and feeds, which, due to the presence of a microorganism or derivative or mutant or analog or fragment thereof as described in connection with the composition of the present invention is, inter glia, capable of specifically binding to *Streptococcus mutans* so as to prevent and/or treat caries. Preferably, the microorganism, mutant, derivative, analog or fragment thereof is a microorganism, mutant, derivative or fragment of the present invention. The additive for foods or drinks includes the additive for nutritious compositions for infants.

The additive for foods can be produced by a general method for producing additives for foods, drinks or feeds. If necessary, additives for general use in foods, drinks or feeds, for example, additives described in Food Additive Handbook (The Japan Food Additives Association; issued on Jan. 6, 1997) may be added satisfactorily, including sweeteners, colorants, preservatives, thickeners and stabilizers, antioxidants, color fixing agents, bleaches, antiseptics, gum base, bitters, enzymes, brightening agents, acidifier, seasonings, emulsifiers, enhancers, agents for manufacture, flavors, and spice extracts. Further, conventional saccharides, starch, inorganic materials, plant powders, excipients, disintegrators, lubricants, binders, surfactants, and plasticizers mentioned previously for pharmaceutical tablets may be added satisfactorily.

The additives include the following additives.

The sweeteners include aspartame, licorice, stevia, xylose and rakanka (Momordica grosvenori fruit). The colorants include carotenoid and turmeric oleoresin, flavonold, caramel color, spirulina color, chlorophyll, purple sweet potato color, purple yam color, perilla color, and blueberry color.

The preservatives include, for example, sodium sulfite, benzoates, benzoin extract, sorbates, and propionates. The thickeners and stabilizers include, for example, gums such as gum arable and xanthan gum, alginates, chitin, chitosan, aloe extract, guar gum, hydroxypropyl cellulose, sodium casein, corn starch. carboxymethyl cellulose, gelatin, agar, dextrin, methyl cellulose, polyvinyl alcohol, microfiber cellulose, microcrystalline cellulose, seaweed cellulose, sodium polyacrylate, sodium polyphosphate, carrageenan or yeast cell wall.

The anti-oxidants include, for example, vitamin C group, sodium ethylenediaminetetraacetate, calcium ethylenediaminetetraacetate, erythorbic acid, oryzanol, catechin, quercetin, clove extract, enzyme-treated rutin, apple extract, sesame seed extract, dibutylhydroxytoluene, fennel extract, horseradish extract, water celery extract, tea extract, tocopherols, rapeseed extract, coffee bean extract, sunflower seed extract, ferulio acid, butylhydroxyanisole, blueberry leaf extract. propolis extract, pepper extract, garden balsam extract, gallic acid, eucalyptus extract, and rosemary extract.

The color fixing agents include, for example, sodium nitrite. The bleaches include, for example, sodium sulfite.

The antiseptics include, for example, o-phenyl phenol. The gum base includes, for example, acetylricinoleate methyl, urushi wax, ester gum, elemi resin, urucury wax, kaurigum, carnaubawax, glycerin fatty acid ester, spermaceti wax, copaibabalsam, copal resin, rubber, rice bran wax, cane wax, shellac, jelutong, sucrose fatty acid ester, depolymerized natural rubber, paraffin wax, fir balsam, propylene glycol fatty acid ester, powdered pulp, powdered rice hulls, jojoba oil, polyisobutylene, polybutene, microcrystalline wax, mastic gum, bees wax and calcium phosphate.

The bitters include, for example, iso-alpha-bitter acid, caffeine, kawaratake (*Coriolus versieolor*) extract, redbark cinchona extract, Phellodendron bark extract, gentian root extract, spice extracts, enzymatically modified naringin, Jamaica cassia extract, theabromine, naringin, cassia extract, absinth extract, isodonis extract, olive tea, bitter orange (*Citrus aurantium*) extract, hop extract and wormwood extract.

The enzymes include, for example, amylase, trypsin or rennet.

The brightening agents include, for example, urushi wax and japan wax. The acidifier include, for example, adipic acid, itacania acid, citric acids, succinic acids, sodium acetate, tartaric acids, carbon dioxide, lactic acid, phytic acid, fumario acid, malic acid and phosphoric acid. The seasonings include, for example, amino acids such as asparagine, aspartic acid, glutamic acid, glutamine, alanine, isoleucine, glycine, serine, cystine, tyrosine, leucine, and praline, nucleic acids such as sodium inosinate, sodium uridinate, sodium guanylate, sodium cytidylate, calcium ribonucleotide and sodium ribonucleotide, organic acids such as citric acid and succinic acid, potassium chloride, sodium chloride-decreased brine, crude potassium chloride, whey salt, tripotassium phosphate, dipotassium hydrogen phosphate, potassium dihydrogen phosphate, disodium hydrogen phosphate, sodium dihydrogen phosphate, trisodium phosphate and chlorella extract.

The enhancers include, for example, zinc salts, vitamin C group, various amino acids, 5-adenylic acid, iron chloride, hesperidin, various calcined calcium, various non-calcined calcium, dibenzoylthiamine, calcium hydroxide, calcium carbonate, thiamine' hydrochloride salt, Dunallella. Oarotene, tocopherol, nicotinic acid, carrot carotene, palm oil carotene, calcium pantothenate, vitamin A, hydroxyproline, calcium dihydrogen pyrophosphate, ferrous pyrophosphate, ferric pyrophosphate, ferritin, heme iron, menaquinone, folic acid and riboflavine.

The agents for manufacture include, for example, processing auxiliaries such as acetone and ion exchange resin. The flavors include, for example, vanilla essence and the spice extracts include, for example, capsicum extract.

These various additives can be added to the active ingredient, taking into consideration the mode of administration, in accordance with the present invention. The anticariogenic composition of the present invention encompasses an amount of a microorganism or derivative or mutant thereof of the present invention or analog or fragment thereof as described in connection with the composition of the present invention. Preferably, the microorganism, mutant, derivative, analog or fragment thereof is a microorganism, mutant, derivative or fragment of the present invention. It is envisaged that the compositions and in particular the anticariogenic composition comprise a microorganism of the present invention as described in connection with the composition of the present invention in the form of a probiotic microorganism. Namely, in addition to the probiotic effect, the probiotic microorganism of the present invention is useful for treating and/or preventing caries. The amount of said probiotic microorganism is high enough to significantly positively modify the condition to be treated, preferably caries, but low enough to avoid serious side effects (at a reasonable benefit/risk ratio), within the scope of sound medical judgment. An effective amount of said probiotic microorganism will vary with the particular goal to be achieved, the age and physical condition of the patient being treated, the severity of the underlying disease, the duration of treatment, the nature of concurrent therapy and the specific microorganism employed. The effective amount of said probiotic microorganism will thus be the minimum amount which will provide the desired specific binding to *Streptococcus mutans*. The presence of, for example, $1\times10^9$ bacteria, as viable or non-viable whole cells, in 0.05 ml solution of phosphate buffered saline solution, or in 0.05 ml of suspension of agar, or the dry weight equivalent of cell wall fragments, is effective when administered in quantities of from about 0.05 ml to about 20 ml.

A decided practical advantage is that the probiotic organism may be administered in a convenient manner such as by the oral route. Depending on the route of administration, the active ingredients which comprise said probiotic organisms may be required to be coated in a material to protect said organisms from the action of enzymes, acids and other natural conditions which may inactivate said organisms. In order to administer probiotic organisms by other than parenteral administration, they should be coated by, or administered with, a material to prevent inactivation. For example, probiotic organisms may be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport lactobacilli or their by-products to the urogenital surface. Dispersions can also be prepared, for example, in glycerol, liquid polyethylene glycols, and mixtures thereof, and in oils. Generally, dispersions are prepared by incorporating the various sterilized probiotic organisms into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient plus any additional desired ingredient from previously sterile-filtered solution thereof. Additional preferred methods of preparation include but are not limited to lyophilization and heat-drying.

The anticariogenic composition also encompasses products intended to be administered orally, or buccal, which comprise an acceptable pharmaceutical carrier as described herein to which, or onto which, cells of a microorganism of the present invention as described in connection with the composition of the present invention which is preferably a microorganism of the present invention is added in fresh, concentrated or dried form, for example. Of course, also a derivative or fragment of said microorganism can be added or any combination of said microorganism, derivative and/or fragment thereof which are disclosed herein. These products may be provided in the form of an ingestible suspension, a gel, a diffuser, a capsule, a hard gelatin capsule, a syrup, or in any other galenic form known to persons skilled in the art.

When the probiotic organisms are suitably protected as described above, the active compound may be orally administered, for example, with an inert diluent or with an assimilable edible carrier, or it may be enclosed in hard or soft shell gelatin capsule, or it may be compressed into tablets designed to pass through the stomach (i.e., enteric coated), or it may be incorporated directly with the food of the diet. For oral therapeutic administration, the probiotic organisms may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains, for example, about $1 \times 10^9$ viable or non-viable e.g., lactobacilli per ml. The probiotic organism is compounded for convenient and effective administration in effective amounts with a suitable pharmaceutically or food acceptable carrier in dosage unit form as hereinbefore disclosed, A unit dosage form can, for example, contain the principal active compound in an amount approximating $10^9$ viable or non-viable, e.g., lactobacilli, per ml. In the case of compositions containing supplementary ingredients such as prebiotics, the dosages are determined by reference to the usual dose and manner of administration of the said ingredients.

The Figures show:

FIG. 1: Aggregation of *Streptococcus mutans* by *Lactobacillus* species

The figure shows a mixture of an aggregating *Lactobacillus* with *S. mutans* (left tube) in comparison with a mixture of a non-aggregating *Lactobacillus* with *S. mutans* (right tube). The experiment has been performed as described in Example 3 and the tubes were left undisturbed for 20 minutes to allow the aggregates to settle.

Figure 2:
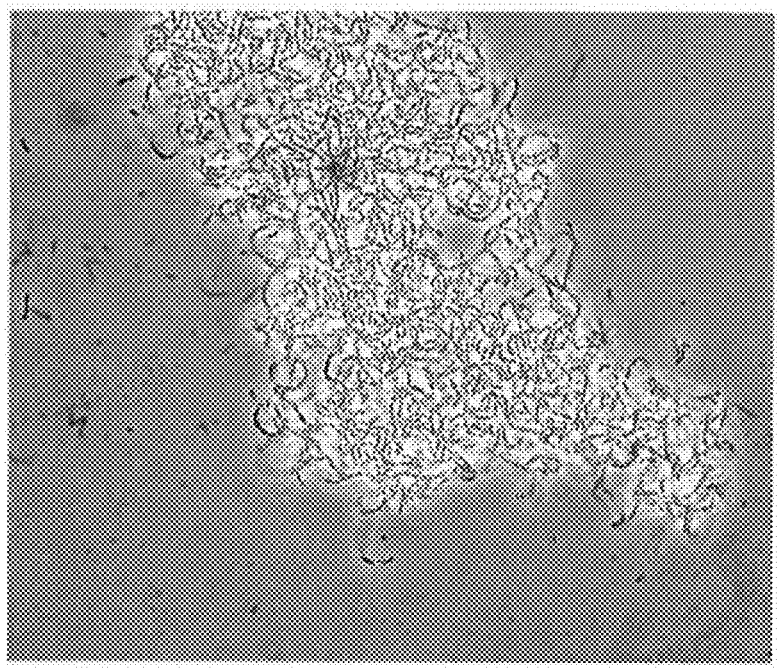

FIG. 2: Microscopic picture of an aggregating *Lactobacillus* species with *Streptococcus mutans*

The figure shows a microscopic picture of the aggregate between *Lactobacillus* and *S. mutans* shown in FIG. 1 (left tube). The picture was taken at a 1000-fold magnification using a phase-contrast microscope.

A better understanding of the present invention and of its many advantages will be had from the following examples, offered for illustrative purposes only, and are not intended to limit the scope of the present invention in any way.

EXAMPLE 1: STORAGE AND GROWTH

Storage and growth of strains can occur according to ordinary procedures. For example, strains can be stored as frozen stocks at −80° C. 1 ml of a culture can be grown to stationary phase (OD600/mL 4-8) in MRS-Medium and mixed with 500 μl of a sterile 50% glycerine solution and frozen. Cultures of *S. mutans* can be grown in TSY-media to stationary phase (OD600/mL 1-2) and treated as mentioned above.

Cultivation of *S. mutans* (DSMZ 20523, serotype c; NCTC 10923, serotype e; NCTC 11060, serotype f as well as non serotyped isolates) as well as cultivation of lactobacilli can be done in 5 ml in closed FALCON™ centrifuge tubes at 37° C. without shacking over night.

In particular, the strains used in the present application were stored as frozen stocks at −80° C. 1 ml of a culture grown to stationary phase (OD600/mL 4-8) in MRS-broth was mixed with 500 μl of a sterile 50% glycerol solution and frozen.

In particular, cultures of *S. mutans* were grown in TSY-broth to stationary phase (OD600/mL 1-2) and treated as mentioned above.

Cultivation of *S. mutans* (DSMZ 20523, serotype c; NCTC 10923, serotype e; NCTC 11060, serotype f and other non serotyped—isolates isolated by OrganoBalance) and cultivation of lactobacilli was done in 5 ml in closed FALCON™ centrifuge tubes at 37° C. without shacking over night.

EXAMPLE 2: TAXONOMIC CLASSIFICATION OF STRAINS

The taxonomic classification of the strains was done according to their carbohydrate fermentation pattern. This was determined using the API® 50 CH strips (bioMerieux, France) system and analyzed using APILAB PLUS software version 3.3.3 (bioMerieux, France).

EXAMPLE 3: TEST ON AGGREGATION OF *STREPTOCOCCUS MUTANS*

Mixing of the lactobacilli with *S. mutans* was done in volumetric ratios of 3:1 to 60:1 (*S. mutans*:lactobacilli), this corresponds to a ratio of colony forming units from 1:50 to 1:2,5. An optical density measured at a wavelength of 600 nm in 1 ml means preferably for *S. mutans* $3 \times 10^8$ colony forming units and for lactobacilli preferably $7 \times 10^9$ colony forming units. Mixing was done in 2 mL volume in 15 mL FALCON™ centrifuge tubes. The culture suspensions were diluted with PBS-buffer to obtain the volumetric ratios mentioned above while keeping the final volume at 2 ml. The mixture was vortexed for 15 seconds. An aggregation is visible as an immediate turbidity of the suspension. The tubes were left undisturbed for 20 min, after that period of time the aggregates settle as a visible pellet whereas non-aggregating mixtures stay in suspension.

As a control, self-aggregation of the respective *Lactobacillus* strain and the *S. mutans* strains was always investigated by performing the test with only the *Lactobacillus* or the *S. mutans* strain added to the tube. An aggregation of *S. mutans* by *Lactobacillus* is shown in FIGS. 1 (left tube) and 2.

The lactobacilli strains of the present invention, in particular those deposited with the DSMZ exhibited aggregation of all *S. mutans* serotypes without showing a self-aggregation behaviour.

Media:

| MRS-broth: | |
|---|---|
| MRS-mixture (Difco, USA) | 55 g/L |
| pH: | 6.5 |
| TSY-broth: | |
| TSY-mixture (Difco, USA) | 30 g/L |
| Yeast extract (Deutsche Hefewerke, Germany) | 3 g/L |

Buffer:

| PBS-buffer: | |
|---|---|
| $Na_2HPO_4 \cdot 2H_2O$ | 1.5 g/L |
| $KH_2PO_4$ | 0.2 g/L |
| NaCl | 8.8 g/L | pH adjusted with HCl

EXAMPLE 4: SPECIFICITY OF THE AGGREGATION TOWARDS TYPICAL MEMBERS OF THE ORAL FLORA

The *Lactobacillus* cultures were grown as in Example 1.

The oral bacteria—namely: *Streptococcus salivarius* subsp. *thermophilus* (isolated by OrganoBalance, identified by API® 50 CH strips (Biomerieux, France) according to manufacturers instructions); *Streptococcus oralis* (DSMZ 20066); *Streptococcus oralis* (DSMZ 20395); *Streptococcus oralis* (DSMZ 20627); *Staphylococcus epidermidis* (DSMZ 1798); *Staphylococcus epidermidis* (DSMZ 20044); *Streptococcus mitis* (DSMZ 12643); *Streptococcus sanguinis* (DSMZ 20567)—were grown in 5 mL BHI-medium in closed 15 mL FALCON™ centrifuge tubes at 37° C. over night. Each of the oral bacteria were preferably mixed in a volumetric ratio of 3:1 with *Lactobacillus* cultures and aggregation was assayed as in Example 3. For each testing of aggregation/non-aggregation only one of the aforementioned bacteria is preferably used to immediately determine the outcome of the testing.

As a control, a self-aggregation of the respective oral bacteria as well as the tested *Lactobacillus* strains was always investigated by performing the test with only the lactobacilli or the oral flora strains added to the tube.

The mentioned *L. paracasei* subsp. *paracasei* strains did not aggregate the oral bacteria mentioned above. The *L. rhamnosus* strains aggregated *Streptococcus salivarius* subsp *thermophilus*.

| BHI-broth: | |
| --- | --- |
| BHI-mixture (Difco, USA) | 37 g/L |
| pH: | 7.2 |

EXAMPLE 5: TEMPERATURE RESISTANCE OF THE AGGREGATING CAPACITY OF THE LACTOBACILLI

The bacteria were grown as in Example 1.

The grown lactobacilli cultures were incubated at 121° C. at 2 bar in satured steam for 20 min (autoclaved). After cooling of the autoclaved cultures to room temperature, the lactobacilli were mixed in a volumetric ratio of 1:3 with grown *S. mutans* cultures and aggregation was assayed as in example 3 including the control experiments. Aggregation was also assayed using the oral bacteria as outlined in Example 4.

It was found that the aggregation behaviour of the lactobacilli was not changed by the autoclaving procedure towards the tested *S. mutans* serotypes or towards the oral bacteria.

EXAMPLE 6: DEPENDENCY OF THE AGGREGATION ON PH-VALUE

The bacteria were grown as in Example 1.

0.5 ml of the lactobacilli and 1.5 ml of *S. mutans* were harvested by centrifugation at 3200*g for 10 min and the supernatant was discarded. The cells were resuspended in their original volume (0.5 ml and 1.5 ml, respectively) in different PBS-buffers adjusted to different pH-values. The pH-values of the buffers were adjusted to values from 7.0 to 3.0 in steps of 0.5 pH-units. Cultures were resuspended in buffers of the respective pH-value that was to be used for the aggregation behaviour assay.

Afterwards the lactobacilli were preferably mixed in a volumetric ratio of 1:3 with *S. mutans* cultures and aggregation was assayed as in example 3 including the control experiments. No visible aggregation of *S. mutans* by the lactobacilli occurred at pH values lower than 4.5.

EXAMPLE 7: SENSITIVITY OF THE AGGREGATION BEHAVIOUR TO LYOPHILISATION

The bacteria were grown as in Example 1.

Aliquots of 1 ml of the lactobacilli cultures were harvested by centrifugation at 3200*g for 10 minutes. The supernatant was discarded and the pellets were lyophilised at room temperature under vacuum for two hours. Resulting dry pellets of each tested *Lactobacillus* strain were stored at room temperature and at 4° C., respectively, for 1 day, 1 week, 2 weeks, 3 weeks and 4 weeks. After the storage time, lyophilised pellets were resuspended in 1 ml PBS-buffer, pH 7.0. The resuspended lactobacilli were mixed in a volumetric ratio of 1:3 with freshly grown *S. mutans* cultures and aggregation was assayed as in example 3 including the control experiments.

The aggregation behaviour of the mentioned lactobacilli towards *S. mutans* was not changed by the lyophilization or the storage procedures.

EXAMPLE 8: TEST ON PROTEASE RESISTANCE

The bacteria were grown as in Example 1.

Proteases used were Pronase E, Proteinase K, Trypsin, Chymotrypsin (all obtained from Sigma, Germany). Aliquots of 1 ml of the lactobacilli were washed in PBS-buffer by harvesting the cells by centrifugation at 3200*g for 10 minutes and resuspending the pellet in 1 ml PBS-buffer (pH 7.0). Afterwards the cells were harvested again as described above and resuspended in PBS-buffer (pH 7.0) containing the respective protease at a final concentration of 2.5 mg/mL. The suspension was incubated for 1 hour at 37° C. Afterwards the cells were washed and resuspended in PBS-buffer (pH 7.0) as described above.

The aggregation was assayed as in example 3 including the control experiments.

The aggregation behaviour of the mentioned lactobacilli towards *S. mutans* was not changed by treatment with any of the mentioned proteases.

EXAMPLE 9: ION DEPENDENCY OF THE AGGREGATION BEHAVIOUR

The bacteria were grown as in Example 1.

Aliquots of 1 ml of the lactobacilli were washed in 1 ml 200 mM EDTA solution twice as described above. Afterwards the cells were harvested and resuspended in 1 ml PBS-buffer (pH 7.0).

The aggregation was assayed as in Example 3 and a complete loss of the aggregation ability was observed. Resuspension of the lactobacilli in 1 mi of a 2 mM calcium solution after the two times washing in 200 mM EDTA-solution restored the ability to aggregate *S. mutans*. Resuspension of the EDTA washed cells in up to 100 mM magnesium solution did not restore the ability to aggregate *S. mutans*.

EXAMPLE 10: TEST OF AGGREGATION IN THE PRESENCE OF SALIVA

The bacteria were grown as in Example 1.

2 ml aliquots of *S. mutans* cultures were harvested as described above and resuspended in 2 ml of saliva. The saliva was provided by two volunteers and used immediately after winning.

The aggregation was assayed as in Example 3.

The aggregation behaviour of the mentioned lactobacilli towards *S. mutans* did not change in the presence of saliva.

EXAMPLE 11: LOZENGE COMPOSITION (I)

The lozenge composition is preferably prepared as is described in Example 4 on page 8 of DE-C236 45 147, wherein, in addition to the ingredients mentioned in said Example 4, the microorganism of the present invention is added in an amount of $10^2$ to $10^{12}$, preferably $10^3$ to $10^8$ cells per mg of the lozenge.

EXAMPLE 12: LOZENGE COMPOSITION (II)

The lozenge composition is preferably prepared as is described in Example 5 on page 8 of DE-C2 36 45 147, wherein, in addition to the ingredients mentioned in said Example 4, the microorganism of the present invention is added in an amount of $10^2$ to $10^{12}$, preferably $10^3$ to $10^8$ cells per mg of the lozenge.

EXAMPLE 13: DENTIFRICE COMPOSITION

The dentifrice composition is preferably prepared as is described in Example 3 on page 8 of DE-C2 36 45 147, wherein, in addition to the ingredients mentioned in said Example 4, the microorganism of the present invention is added in an amount of $10^2$ to $10^{12}$, preferably $10^3$ to $10^8$ cells per mg of the dentifrice.

EXAMPLE 14: CHALK-BASED DENTIFRICE COMPOSITION

The chalk-based dentifrice composition is preferably prepared as is described in chapter 7.1.4.4 "Rezepturbeispiel" on page 205 of the textbook "Kosmetik", W. Umbach (editor), $2^{nd}$ edition, Thieme Verlag, 1995, wherein, in addition to the ingredients mentioned in said chapter on page 205, the microorganism of the present invention is added in an amount of $10^2$ to $10^{12}$, preferably $10^3$ to $10^8$ cells per mg of the chalk-based dentifrice.

EXAMPLE 15: GEL-DENTIFRICE ON BASIS OF SILICIC ACID/SODIUM FLUORIDE

The gel-dentifrice on basis of silicic acid/sodium fluoride dentifrice composition is preferably prepared as is described in chapter 7.1.4.4 "Rezepturbeispiel" on page 205 of the textbook "Kosmetik", W. Umbach (editor), $2^{nd}$ edition, Thieme Verlag, 1995, wherein, in addition to the ingredients mentioned in said chapter on page 205, the microorganism of the present invention is added in an amount of $10^2$ to $10^{12}$, preferably $10^3$ to $10^8$ cells per mg of the gel-dentifrice on basis of silicic acid/sodium fluoride.

EXAMPLE 16: DENTIFRICE COMPOSITION AGAINST TARTAR

The dentifrice composition against tartar is preferably prepared as is described in chapter 7.1.4.4 "Rezepturbeispiel" on page 206 of the textbook "Kosmetik", W. Umbach (editor), $2^{nd}$ edition, Thieme Verlag, 1995, wherein, in addition to the ingredients mentioned in said chapter on page 206, the microorganism of the present invention is added in an amount of $10^2$ to $10^{12}$, preferably $10^3$ to $10^8$ cells per mg of the dentifrice against tartar.

EXAMPLE 17: CHEWING GUM COMPOSITION

The chewing gum composition is preferably prepared as is described in Example 6 on page 9 of DE-02 36 45 147, wherein, in addition to the ingredients mentioned in said Example 4, the microorganism of the present invention is added in an amount of $10^2$ to $10^{12}$, preferably $10^3$ to $10^8$ cells per mg of the chewing gum.

EXAMPLE 18: CONCENTRATED MOUTHWASH COMPOSITION

The concentrated mouth wash composition is preferably prepared as is described in chapter 7.1.4.4 "Rezepturbeispiel" on page 206 of the textbook "Kosmetik", W. Umbach (editor), $2^{nd}$ edition, Thieme Verlag, 1995, wherein, in addition to the ingredients mentioned in said chapter on page 206, the microorganism of the present invention is added in an amount of $10^2$ to $10^{13}$, cells per ml of the concentrated mouthwash composition.

EXAMPLE 19: FILM PREPARATION

Preparation of Films:

1. water phase heat water to 60° C.

aspartame (sweetener) is added under stirring aspartame is dissolved completely a polymeric water-soluble film former, like, for example, KOLLICOAT® IR copolymer (polyethylenglycol on polyvinylalcohol) or PVP (polyvinylpyrrolidon) or natural polymers such as alginates are added under stirring until they are dissolved after 10 min. the rest of the foam is removed the microorganism of the present invention in an amount of $10^2$ to $10^{12}$, preferably $10^3$ to $10^8$ cells per final aroma film is added after cooling down of the mixture;

alternatively, the mutant or derivative of the microorganism of the present invention or an analog or fragment of the microorganism of the present invention can be added.

2. oily phase menthol is dissolved in peppermint-oil polysorbat 80 is added to the peppermint-oil menthol mix under stirring this mixture is then added to propylene-glykole under stirring optional colorants (such as pigments, lakes) can be added

3.

under stirring the oily phase is slowly mixed with the water phase

4.

the thin films are mechanically generated using a cutting device

Sample Formulations:

|  | formulation I weight [g] | composition in film [%] | formulation II weight [g] | composition in film [%] |
|---|---|---|---|---|
| Phase I | | | | |
| aspartame | 0.7 | 1.4 | 0.7 | 1.8 |
| KOLLICOAT® IR | 35.0 | 68.5 | 25.0 | 65.8 |
| ascorbic acid | — | — | 1.0 | 2.6 |
| cherry flavour | — | — | 6.0 | 15.8 |
| water demin. | 85.0 | — | 80.0 | — |
| Phase II | | | | |
| menthol | 1.4 | 2.7 | — | — |
| peppermint oil | 5.6 | 11.0 | — | — |
| polysorbat 80 | 0.7 | 1.4 | — | — |
| propylene glykol | 7.0 | 13.7 | 5.0 | 13.2 |
| green lake | 0.7 | 1.4 | — | — |
| azorubin lake | — | — | 0.3 | 0.8 |
| sum | 136.1 | 100.0 | 118.0 | 100.0 |
| solid content | 51.1 | | 38.0 | |

Other embodiments and uses of the invention will be apparent to those skilled in the art from consideration of the specification and practice of the invention disclosed herein. All references cited herein, for any reason, including all publications, all U.S: and foreign patents and all U.S. and foreign patent applications, are specifically and entirely incorporated by reference for all purposes. It is intended that the specification and examples be considered exemplary only with the true scope and spirit of the invention indicated by the following claims.

The invention claimed is:

1. A liquid or solid composition comprising cells of at least one microorganism belonging to *Lactobacillus paracasei* which is thermally inactivated by heating at more than 95° C. for at least 20 minutes, wherein all cells of at least one microorganism belonging to *Lactobacillus paracasei* in the liquid or solid composition are dead or inactivated cells, wherein said cells bind to *Streptococcus mutans* in the presence of saliva or at a pH range between 4.5 and 8.5,
wherein the binding between said cells and *Streptococcus mutans* is calcium-dependent, resistant to heat treatment at more than 95° C. for at least 20 minutes, and resistant to protease treatment,
and
wherein the composition comprises the cells in an amount of at least 0.001% by weight based on the weight of the composition;
wherein said composition optionally comprises less than 1% (w/w) lactose or more than 6% (w/w) lactose based on the composition;
wherein the composition is an animal feed which further comprises at least one orally acceptable carrier or excipient; and
wherein the microorganism is selected from the group consisting of *L. paracasei* DSM 16667, *L. paracasei* DSM 16668, *L. paracasei* DSM 16669, *L. paracasei* DSM 16670, and *L. paracasei* DSM 16671.

2. The composition of claim 1, wherein the feed composition is a pet feed for dogs, cats, and rats, a cattle feed for cows and pigs, chicken feed for chicken and turkeys, or a fish cultivation feed for porgy and yellowtail.

3. The composition of claim 1, wherein the at least one orally acceptable carrier or excipient comprises a raw feed material selected from the group consisting of cereals, brans, oil-seed meals, animal-derived raw feed materials, and combinations thereof.

4. The composition of claim 1, wherein the at least one orally acceptable carrier or excipient comprises a cereal selected from the group consisting of mile, wheat, barley, oats, rye, brown rice, buckwheat, fox-tail millet, Chinese millet, Deccan grass, corn, soybean, and combinations thereof.

5. The composition of claim 1, wherein the at least one orally acceptable carrier or excipient comprises a bran selected from the group consisting of rice bran, defatted rice bran, bran, lowest-grade flour, wheat germ, barley bran, screening pellet, corn bran, corn germ, and combinations thereof.

6. The composition of claim 1, wherein the at least one orally acceptable carrier or excipient comprises an oil-seed meal selected from the group consisting of soybean meal, soybean powder, linseed meal, cottonseed meal, peanut meal, safflower meal, coconut meal, palm meal, sesame meal, sunflower meal, rapeseed meal, kapok seed meal, mustard meal, and combinations thereof.

7. The composition of claim 1, wherein the at least one orally acceptable carrier or excipient comprises an animal-derived raw feed material selected from the group consisting of fish powders, meat powder, meat and bone powder, blood powder, bone powder, byproducts from butchery, feather meal, silkworm pupa, skim milk, casein, dry whey, hill, and combinations thereof.

8. The composition of claim 1, wherein the at least one orally acceptable carrier or excipient comprises a raw feed material selected from the group consisting of plant stems and leaves, byproducts from corn processing industries, starch, sugar, yeast, byproducts from fermentation, agricultural byproducts, and combinations thereof.

9. The composition of claim 1, wherein the composition has anticariogenic activity.

10. The composition of claim 1, wherein the formation of aggregates of the microorganism and *Streptococcus mutans* occurs in the presence of saliva or at a pH range between 4.5 and 8.5.

11. The composition of claim 1, wherein the composition comprises at least 0.01% by weight of the cells.

12. The composition of claim 1, wherein the composition comprises at least 0.1% by weight of the cells.

13. The composition of claim 1, wherein the microorganism binds to *Streptococcus mutans* serotype c (DSMZ 20523) and/or serotype e (NCTC 10923) and/or serotype f (NCTC 11060).

14. A method for the production of the composition according to claim 1 comprising obtaining the cells of a microorganism belonging to the group of lactic acid bacteria, and adding said cells to a raw or cooked feed material, molding, and granulating to form the composition.

15. A liquid or solid composition comprising cells of at least one microorganism belonging to *Lactobacillus paracasei* which is thermally inactivated by heating at more than 95° C. for at least 20 minutes, the cells consisting of dead or inactivated cells, wherein said cells bind to *Streptococcus mutans* in the presence of saliva or at a pH range between 4.5 and 8.5,
wherein the binding between said cells and *Streptococcus mutans* is calcium-dependent, resistant to heat treatment at more than 95° C. for at least 20 minutes, and resistant to protease treatment,
and wherein the composition comprises the cells in an amount of at least 0.001% by weight based on the weight of the composition;
wherein said composition optionally comprises less than 1% (w/w) lactose or more than 6% (w/w) lactose based on the composition;
wherein the composition is a food or drink which further comprises at least one orally acceptable carrier or excipient; and
wherein the microorganism is selected from the group consisting of *L. paracasei* DSM 16667b1946, *L. paracasei* DSM 16668b1946, *L. paracasei* DSM 16669b1946, *L. paracasei* DSM 16670b1946, and *L. paracasei* DSM 16671b1946.

16. The composition of claim 15, wherein the food or drink is selected from the group consisting of juices, refreshing drinks, soups, teas, sour milk beverages, dairy products, ices, butter, cheese, processed milk, skim milk, meat products, fish meat cake products, egg products, confectioneries, breads, noodles, pickles, smoked products, dried fishes, and seasonings.

17. The composition of claim 15, wherein the composition is a powder food, sheet-like food, bottled food, canned food, retort food, capsule food, tablet food, or fluid food.

18. The composition of claim 15, wherein the composition comprises at least 0.01% by weight of the cells.

19. The composition of claim 15, wherein the composition comprises at least 0.1% by weight of the cells.

20. The composition of claim 15, wherein the microorganism binds to *Streptococcus mutans* serotype c (DSMZ 20523) and/or serotype e (NCTC 10923) and/or serotype f (NCTC 11060).

21. A method for the production of the composition according to claim 15 comprising obtaining the cells of a microorganism belonging to the group of lactic acid bacteria, and adding said cells to a raw or cooked feed material, molding, and granulating to form the composition.

22. A liquid or solid composition comprising cells of at least one microorganism belonging to *Lactobacillus paracasei* which is thermally inactivated by heating at more than 95° C. for at least 20 minutes, wherein all cells of at least one microorganism belonging to *Lactobacillus paracasei* in the liquid or solid composition are dead or inactivated cells, wherein said cells bind to *Streptococcus mutans* in the presence of saliva or at a pH range between 4.5 and 8.5,
wherein the binding between said cells and *Streptococcus mutans* is calcium-dependent, resistant to heat treatment at more than 95° C. for at least 20 minutes, and resistant to protease treatment,
and
wherein the composition comprises the cells in an amount of at least 0.001% by weight based on the weight of the composition;
wherein said composition optionally comprises less than 1% (w/w) lactose or more than 6% (w/w) lactose based on the composition;
wherein the composition is an animal feed which further comprises at least one orally acceptable carrier or excipient; and
wherein the microorganism is selected from the group consisting of *L. paracasei* DSM 16667b1946, *L. paracasei* DSM 16668b1946, *L. paracasei* DSM 16669b1946, *L. paracasei* DSM 16670b1946, and *L. paracasei* DSM 16671b1946; and
wherein the at least one orally acceptable carrier or excipient is selected from the group consisting of fluoride ion sources, anticalculus agents, buffers, abrasive materials, peroxide sources, alkali metal bicarbonate salts, thickening materials, humectants, surfactants, titanium dioxide, flavor agents, sweetening agents, xylitol, coloring agents, starch, glucose, sucrose, gelatin, malt, rice, flour, chalk, silica gel, sodium stearate, glycerol monostearate, talc, sodium ions, dried skim milk, glycerol, propylene glycol, water, ethanol, and mixtures thereof.

* * * * *